United States Patent
Chuang et al.

(10) Patent No.: US 10,246,715 B1
(45) Date of Patent: Apr. 2, 2019

(54) CPG-OLIGODEOXYNUCLEOTIDE, IMMUNOGENIC COMPOSITION INCLUDING THE SAME, AND METHOD OF INDUCING IMMUNE RESPONSE BY THE SAME

(71) Applicant: National Health Research Institutes, Miaoli County (TW)

(72) Inventors: Tsung-Hsien Chuang, Miaoli County (TW); Da-Wei Yeh, Miaoli County (TW); Chao-Yang Lai, Miaoli County (TW); Yi-Ling Liu, Miaoli County (TW); Chih-Hao Lu, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 0 days.

(21) Appl. No.: 15/722,949

(22) Filed: Oct. 2, 2017

(51) Int. Cl.
| | |
|---|---|
| *A61K 39/00* | (2006.01) |
| *A61K 38/19* | (2006.01) |
| *A61K 39/12* | (2006.01) |
| *A61K 39/39* | (2006.01) |
| *A61K 45/06* | (2006.01) |
| *C12N 15/117* | (2010.01) |

(52) U.S. Cl.
CPC ............ *C12N 15/117* (2013.01); *A61K 39/39* (2013.01); *A61K 2039/55561* (2013.01); *C12N 2310/17* (2013.01)

(58) Field of Classification Search
CPC ................ A61K 2300/00; A61K 39/39; A61K 2039/55561; A61K 31/711; A61K 39/0011
See application file for complete search history.

(56) References Cited

FOREIGN PATENT DOCUMENTS

CN    1324661    * 12/2001

OTHER PUBLICATIONS

Brownlie, R. et al. "Chicken TLR21 acts as a functional homologue to mammalian TLR9 in the recognition of CpG oligodeoxynucleotides," Molecular immunology. Jul. 1, 2009; 46(15):3163-70.
Yeh, D.W. et al. "Toll-like receptor 9 and 21 have different ligand recognition profiles and cooperatively mediate activity of CpG-oligodeoxynucleotides in zebrafish," Proceedings of the National Academy of Sciences of the United States of America. Dec. 1, 2013;110(51):20711-6.
Liu, J. "Activation of rabbit TLR9 by different CpG-ODN optimized for mouse and human TLR9," Comparative immunology, microbiology and infectious diseases, Mar. 28, 2012; 35(5):443-51.
Li, Y.W. et al. "Molecular cloning of orange-spotted grouper (*Epinephelus coioides*) TLR21 and expression analysis post Cryptocaryon irritans infection," "Cryptocaryon irritans infection, Fish & shellfish immunology," Nov. 27, 2012; 32(3):476-81.
Chuang, TH, et al. "Development of CpG-Oligodeoxynucleotides for Effective Activation of Rabbit TLR9 Mediated Immune Responses," PLOS one, Sep. 30, 2014;9(9):e108808 pp. 1-8.

\* cited by examiner

*Primary Examiner* — Barry A Chestnut
(74) *Attorney, Agent, or Firm* — Muncy, Geissler, Olds & Lowe, P.C.

(57) ABSTRACT

A CpG-oligodeoxynucleotide (CpG-ODN) for inducing a TLR9 activated immune response, a TLR21 activated immune response or a combination thereof in a host is provided. The CpG-ODN includes one or more copies of the sequences of GTCGTT, one or more copies of the sequences of GTT and one or more copies of the sequences of TTTT, wherein at least one copy of the sequence of GTCGTT is encoded between the sequence of GTT and the sequence of TTTT. Further, an immunogenic composition including the CpG-ODN and a method of inducing immune response by the same are also provided.

15 Claims, 19 Drawing Sheets

Specification includes a Sequence Listing.

```
osgTLR21A   GRIEHVDARIADENYYLLP  979
osgTLR21B   GRIEHVDE----QNYYLLP  975
ggTLR21     GRIEHVDARTSDENYYLLP  979
            ******    : *******
```

FIG. 1F

CPG-OLIGODEOXYNUCLEOTIDE, IMMUNOGENIC COMPOSITION INCLUDING THE SAME, AND METHOD OF INDUCING IMMUNE RESPONSE BY THE SAME

BACKGROUND OF THE INVENTION

1. Field of the Invention

The present invention relates to a CpG-oligodeoxynucleotide (CpG-ODN), an immunogenic composition including the same and methods of inducing immune response by the same, in particular, to a CpG-ODN comprising a GTCGTT motif for inducing a TLR9 activated immune response and/or a TLR21 activated immune response, an immunogenic composition including the same and a method of activating such immune responses.

2. Description of the Related Art

CpG-oligodeoxynucleotides (CpG-ODNs) are known as potent immune modulators which induce the production of inflammatory cytokines and a T helper 1 (Th1) polarized immune response, resulting in the expression of costimulatory molecules in antigen-presenting cells and increased activation of B cells, T cells, NK cells and other immunocytes.

Generally, various CpG-ODNs have species-specific activities based on the compositions and lengths thereof. For instance, CpG-1826 (SEQ ID NO: 4) containing two copies of the GACGTT motif and having a length of 20 nucleotides is more potent in activating murine cells and less effective in activating human cells than CpG-2007 (SEQ ID NO: 11) containing three copies of the GTCGTT motif and having 22 nucleotides. Hence, various kinds of CpG-ODN have been designed and artificially synthesized for inducing the immune responses of a specific receptor in a specific species.

On the other hand, the choices of the target receptor which is activated by the CpG-ODNs may be also a key point to cost down and popularize the CpG-ODNs based treatment. A large number of researchers have found that using Toll-like receptors (TLRs) as a target induced by the CpG-ODNs in a host may be a better choice because of its key role in the innate immune system. For instance, TLR21 in zebrafish (*Danio rerio*), pufferfish (*Takifugu rubripes*) and chicken (*Gallus gallus*) have shown being able to be activated by CpG-ODNs (Brownlie R. et al. Molecular immunology. 2009; 46(15):3163-70).

However, different types of TLRs are expressed in different species, it may cause unnecessary cost on the developments of various types of CpG-ODN appropriating to corresponding species. Hence, developing a single type of CpG-ODN that is able to induce a plurality of types of TLRs, that is, is able to induce the immune responses in different kinds of species and has better activation effects will be a substantial solution of the problem.

SUMMARY OF THE INVENTION

In the present invention, cells of groupers expressing both TLR21 and TLR9, mammals expressing TLR9 are used in the test of activation effects by the CpG-ODNs of the present invention to show that the CpG-ODN is potent to induce the immune responses in different species by activating different types of TLRs.

In the present invention, a CpG-oligodeoxynucleotide (CpG-ODN) for inducing a TLR9 activated immune response, a TLR21 activated immune response or a combination thereof in a host is provided. The CpG-ODN comprises one or more copies of the sequence of GTCGTT, one or more copies of the sequence of GTT and one or more copies of the sequence of TTTT, wherein at least one copy of the sequence of GTCGTT is encoded between the sequence of GTT and the sequence of TTTT.

Preferably, the CpG-ODN comprises the sequence of SEQ ID NO: 1.

Preferably, the CpG-ODN has a length of 19 nucleotides.

Preferably, the CpG-ODN comprises the sequence of SEQ ID NO: 2.

Preferably, the CpG-ODN comprises the sequence of SEQ ID NO: 3.

Preferably, the host is selected from a group consisting of human, ayes, rodent and pisces.

An immunogenic composition for inducing a TLR9 activated immune response, a TLR21 activated immune response or a combination thereof, comprising: the CpG-ODNs mentioned above, and a vehicle, an excipient or a combination thereof.

Preferably, the immunogenic composition further comprises an antigen selected from the group consisting of: virus, bacterium, protozoa, and tumor.

Additionally, a method of inducing an immune response of a host for treating or preventing a disorder is provided, comprising: preparing an immunogenic composition mentioned above which includes an effective dose of CpG-ODN of the present invention; and administrating the immunogenic composition to the host.

Preferably, the host is selected from the group consisting of human, ayes, rodent and pisces.

Preferably, the disorder is selected from the group consisting of breast cancer, prostate cancer, melanoma, lymphoma, non-small-cell lung cancer, basal cell carcinoma, glioblastoma, ovarian cancer, and an infectious disease induced by hepatitis B virus, B. anthrax, malaria, *S. pneumoniae*, herpes simplex virus, influenza virus or a combination thereof.

Preferably, the effective dose is 0.01 mg/kg body weight to 20 mg/kg body weight.

Preferably, the administrating comprises administrating orally or by means of injection.

Preferably, the CpG-ODN of present invention is able to activate both TLR21 and/or TLR9 in a host, that is, is able inducing immune responses in species of human, ayes, rodent, pisces, and other species expressing TLR21 and/or TLR9.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the histograms of appended drawings, the statistics information is as follows: Data represent means±SD (n=3 independent experiments).*P<0.05, **P<0.01 indicates in comparison with a control group.

Figure 1A:
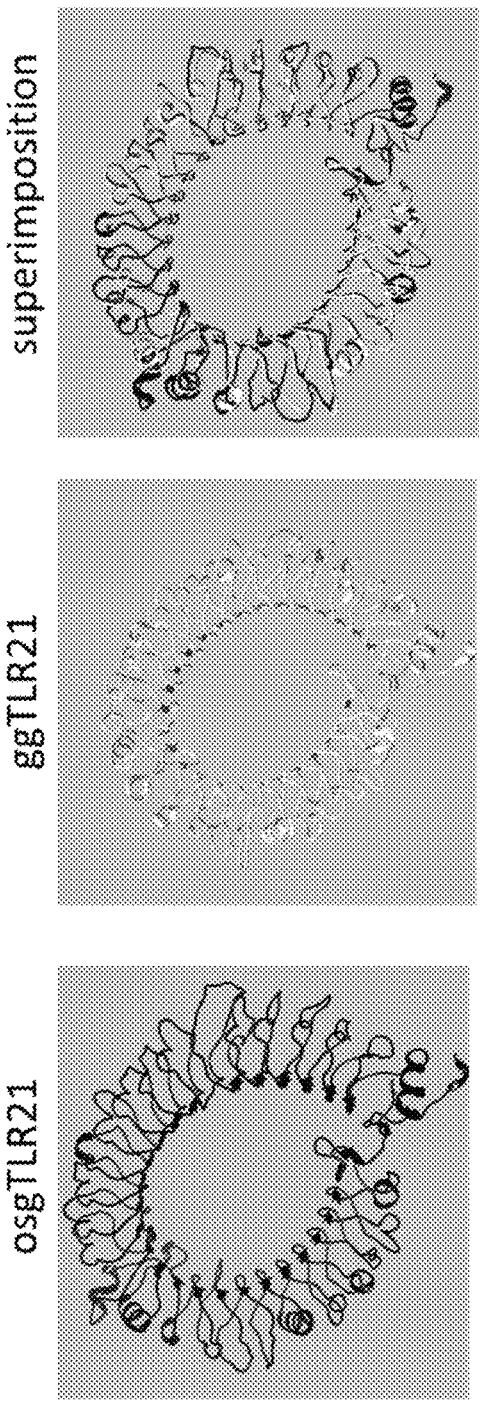

Further, the sequences of the CpG-ODNs labeled in the drawings are shown in Table 1.

Figure 1B:
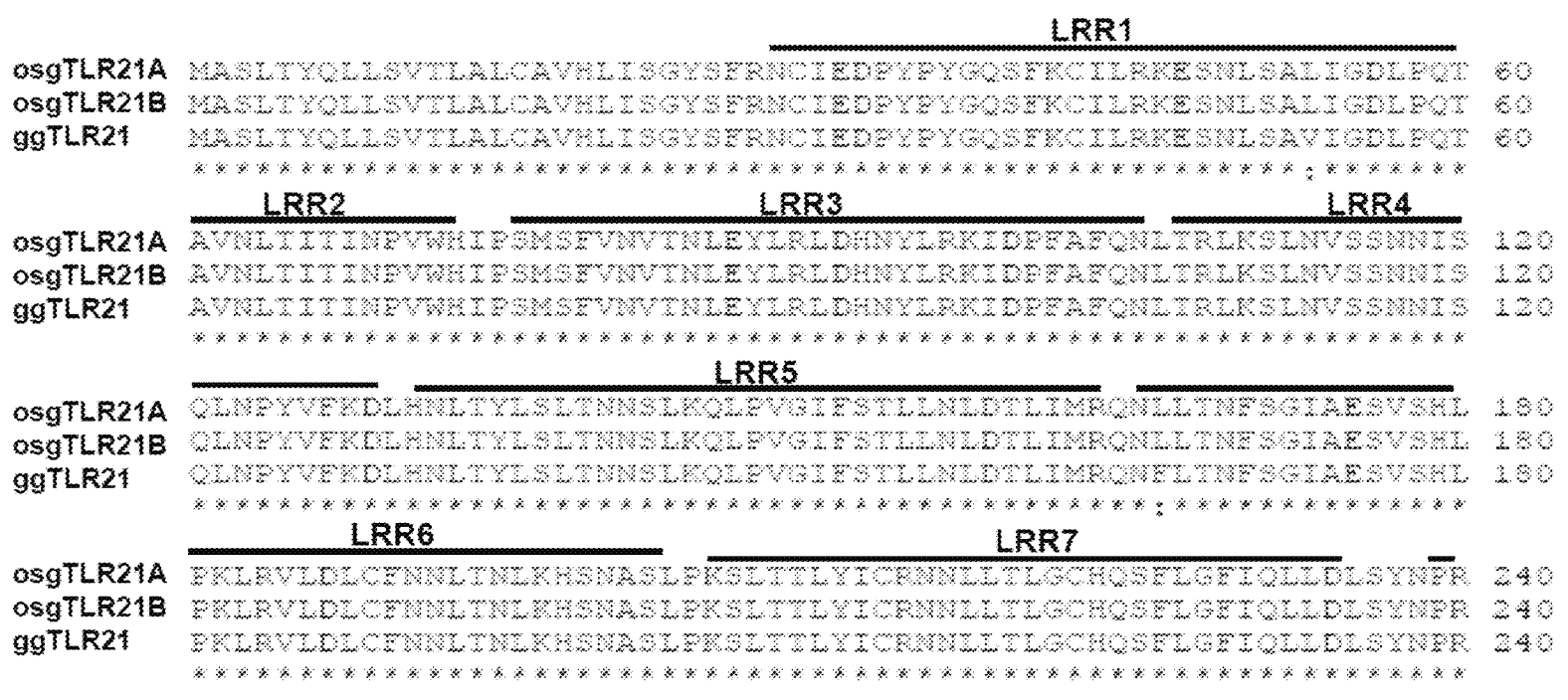
Figure 1C:
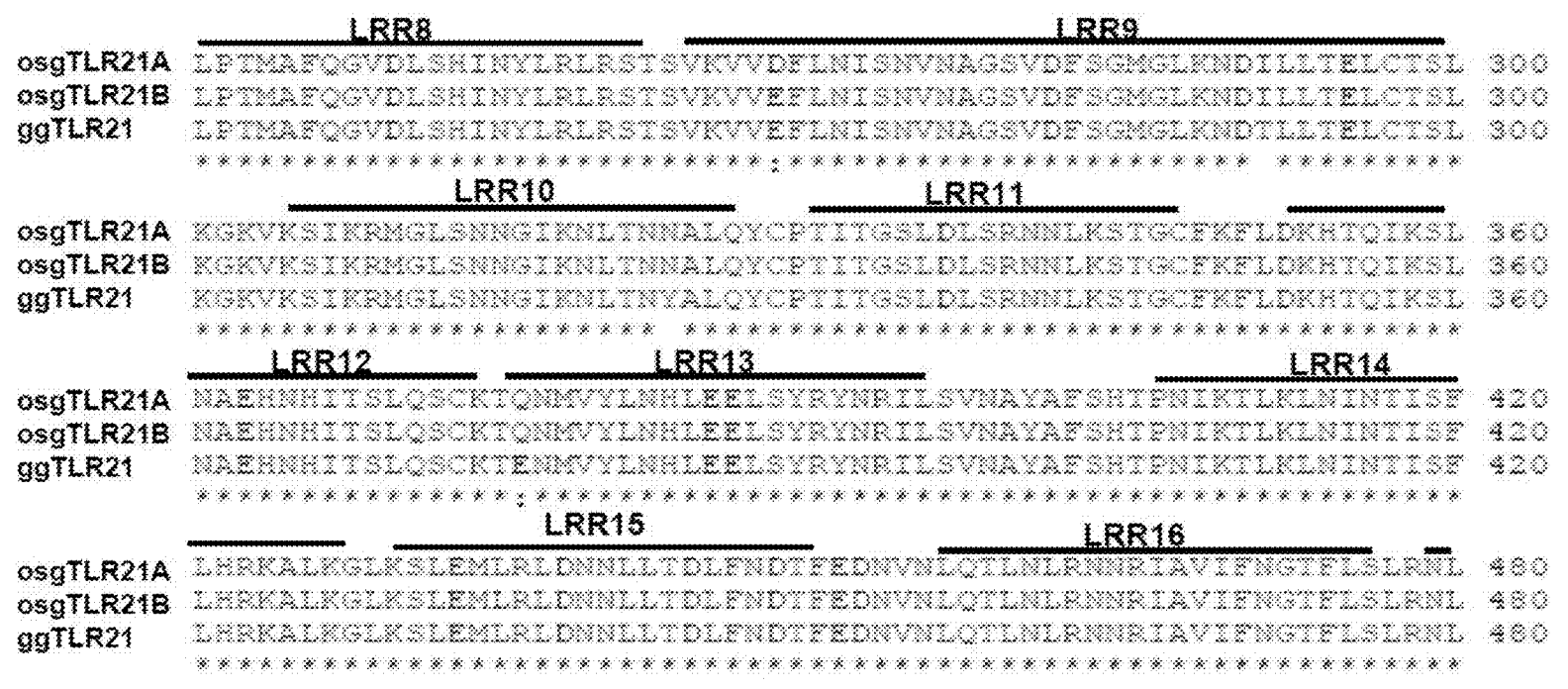
Figure 1D:
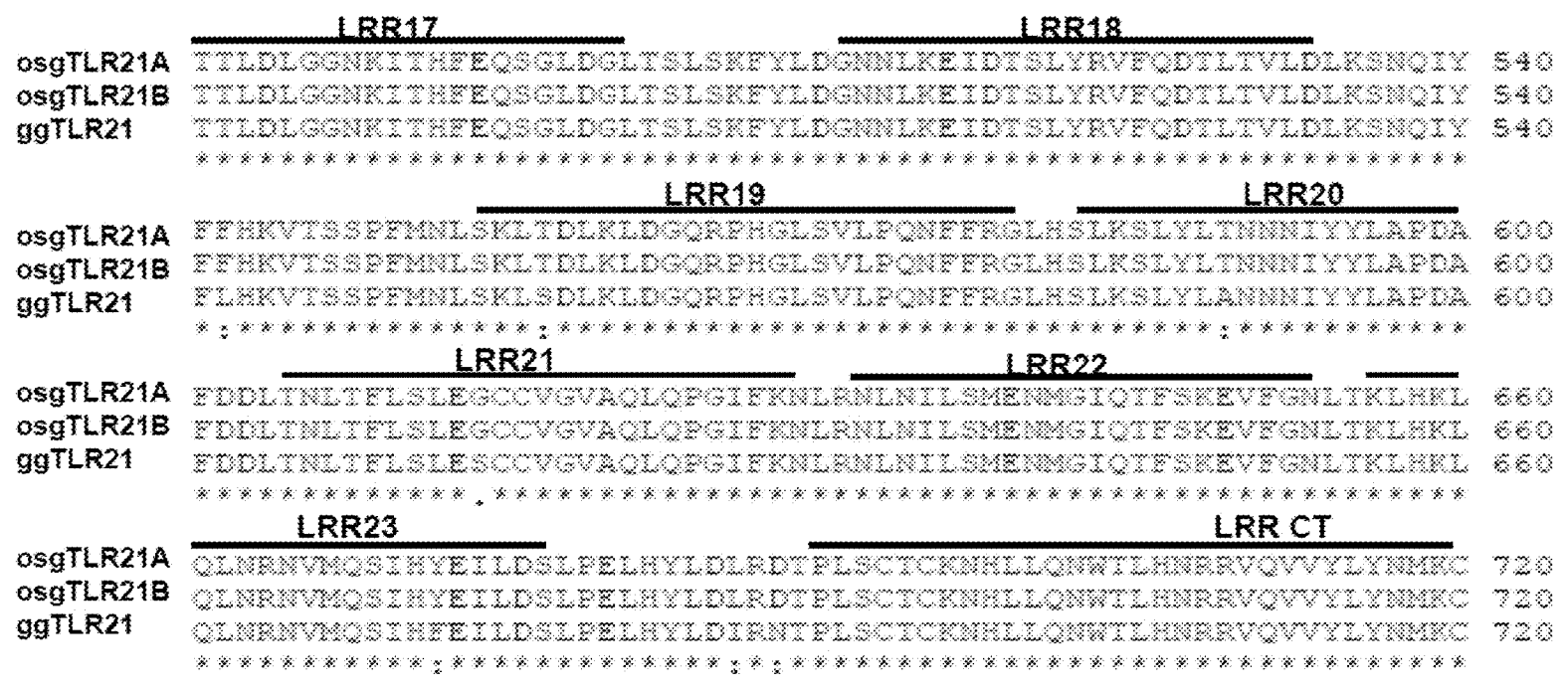
Figure 1E:
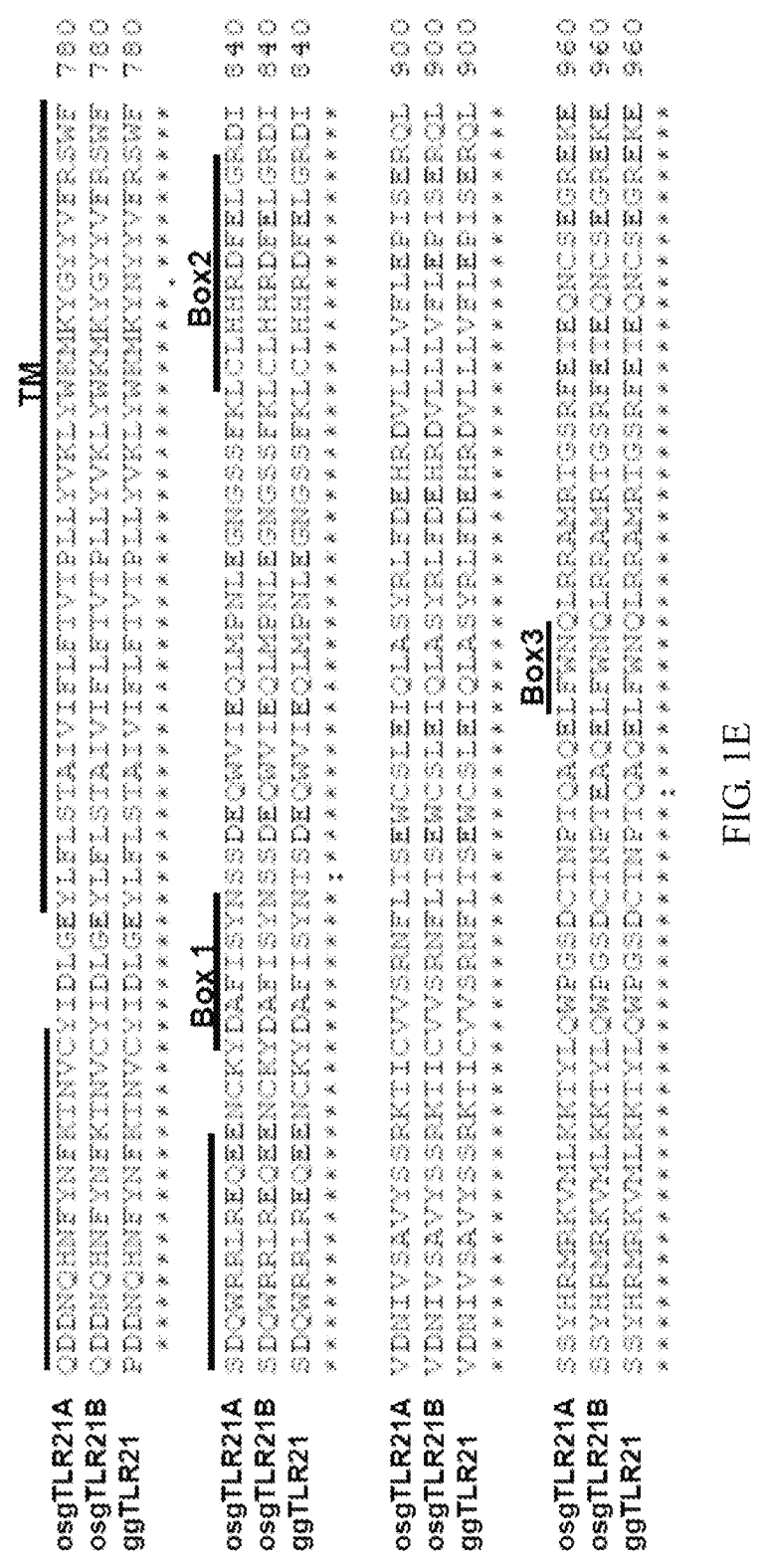

FIG. 1A shows the computational modeling of the ectodomain protein structures of orange-spotted grouper (osg, *E. coioides*) and giant grouper (gg, *E. lanceolatus*) TLR21s.

FIGS. 1B-1F show the protein sequence alignment of osgTLR21A, osgTLR21B, and ggTLR21 Toll/interleukin receptor (TIR) domains.

Figure 2A:
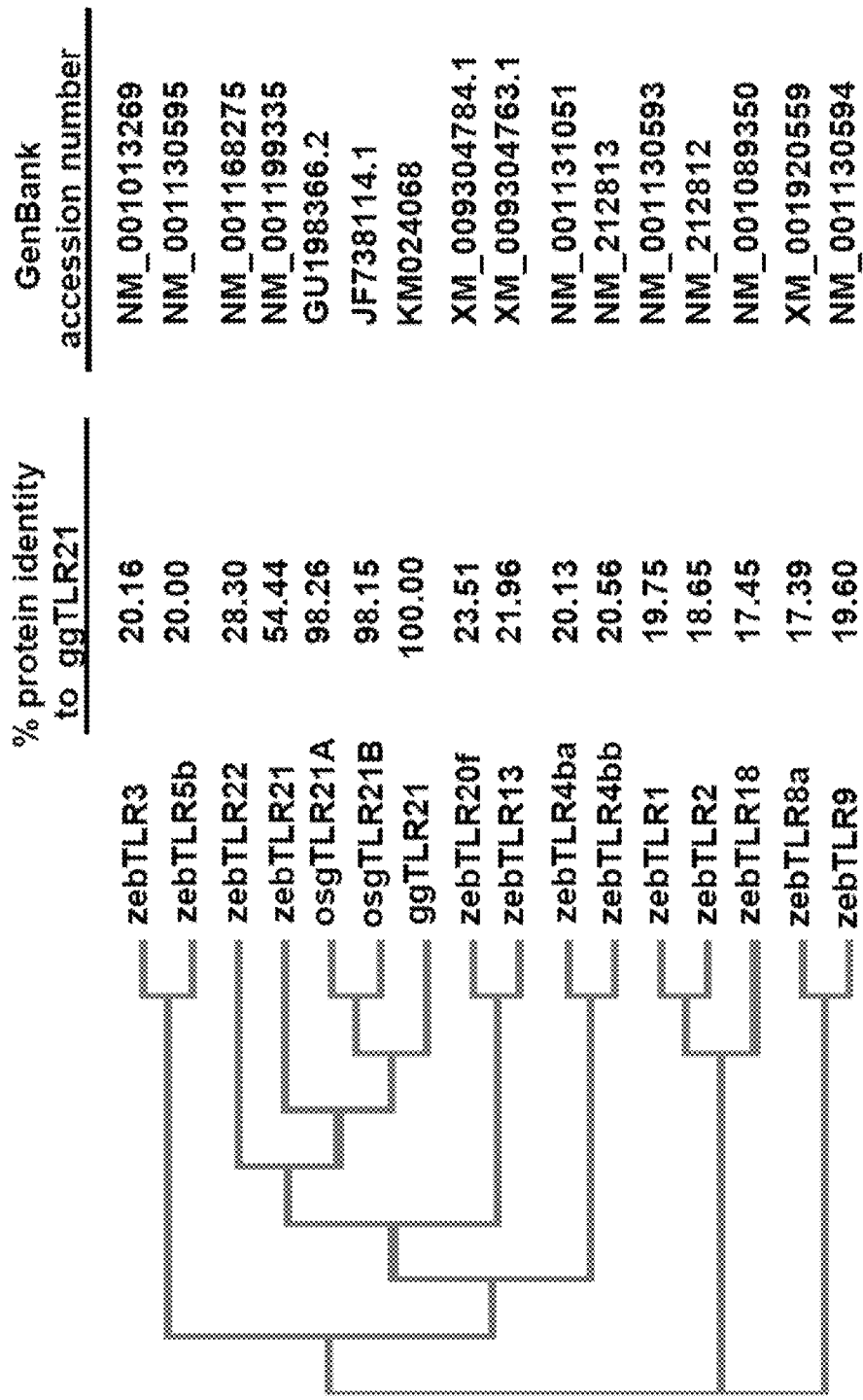
Figure 2B:
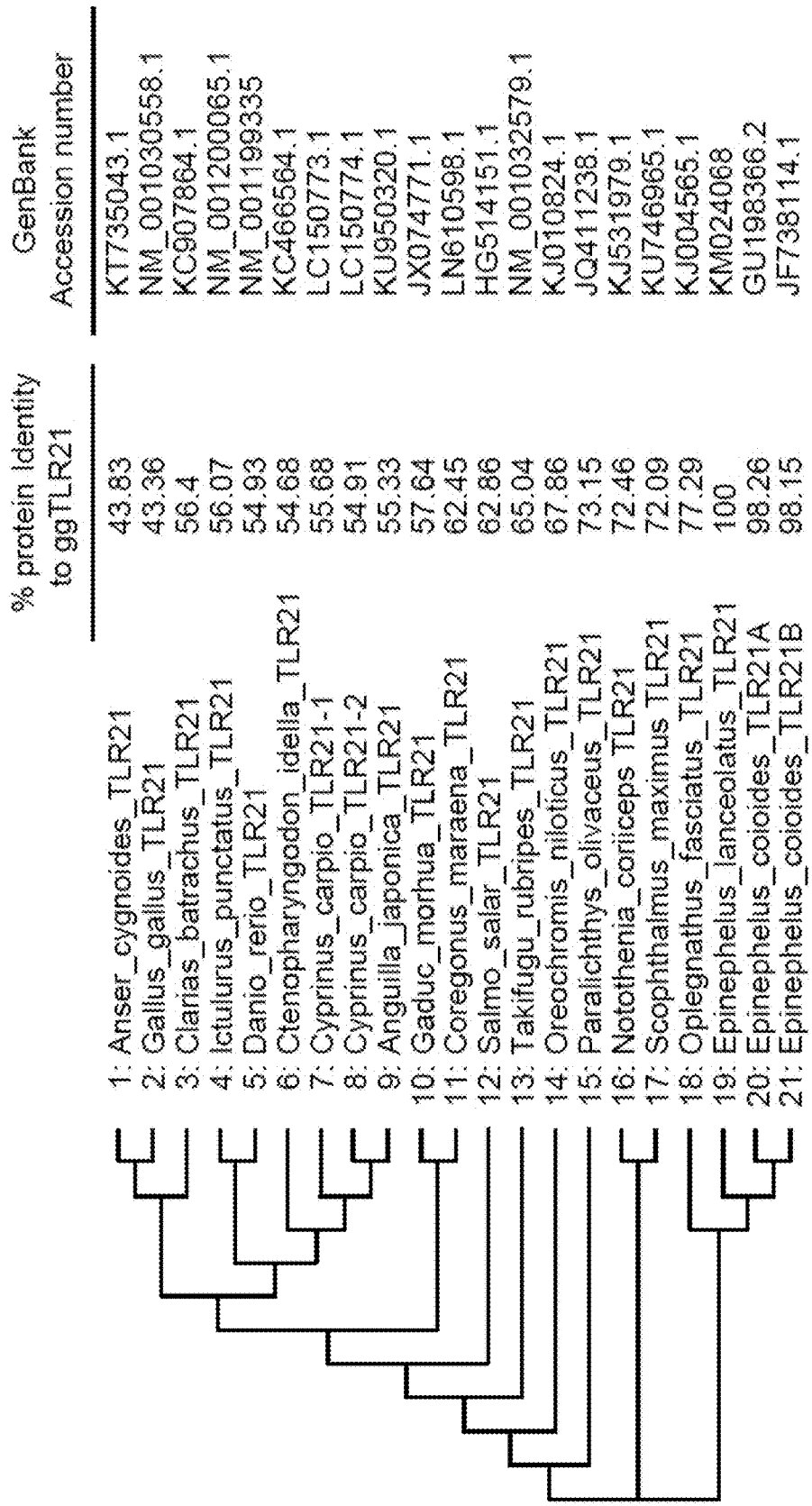

FIGS. 2A and 2B show the protein identity of the protein sequences between ggTLR21 and various TLRs referring to the information obtained from the GenBank database.

Figure 3:
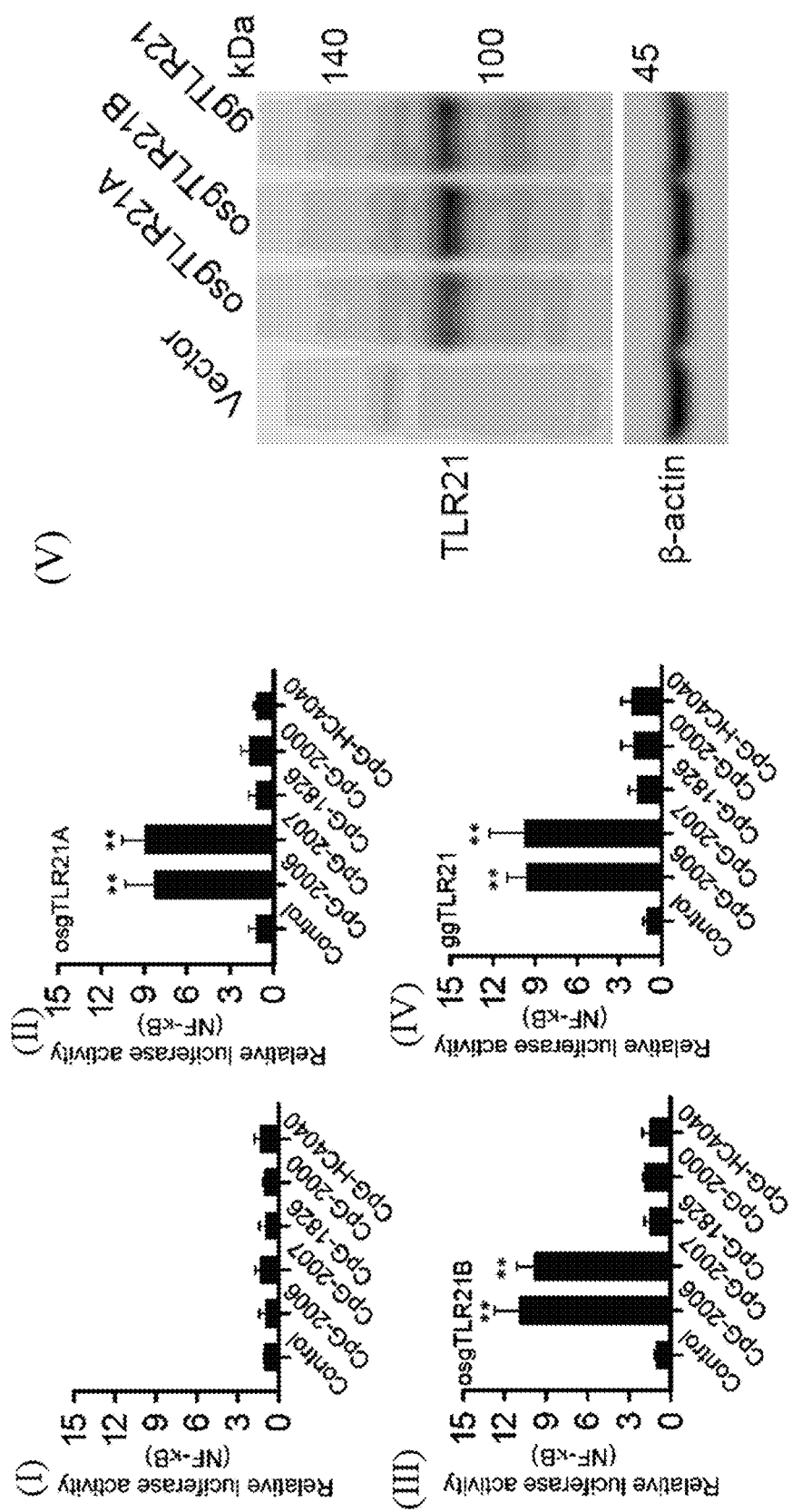

FIG. 3 shows activation of grouper (*Epinephelus* spp.) TLR21 s induced by different types of CpG-ODNs, wherein part (V) of FIG. 3 shows immunoblot analysis results of the expression of the grouper TLR21s using β-actin as a loading control.

Figure 4:
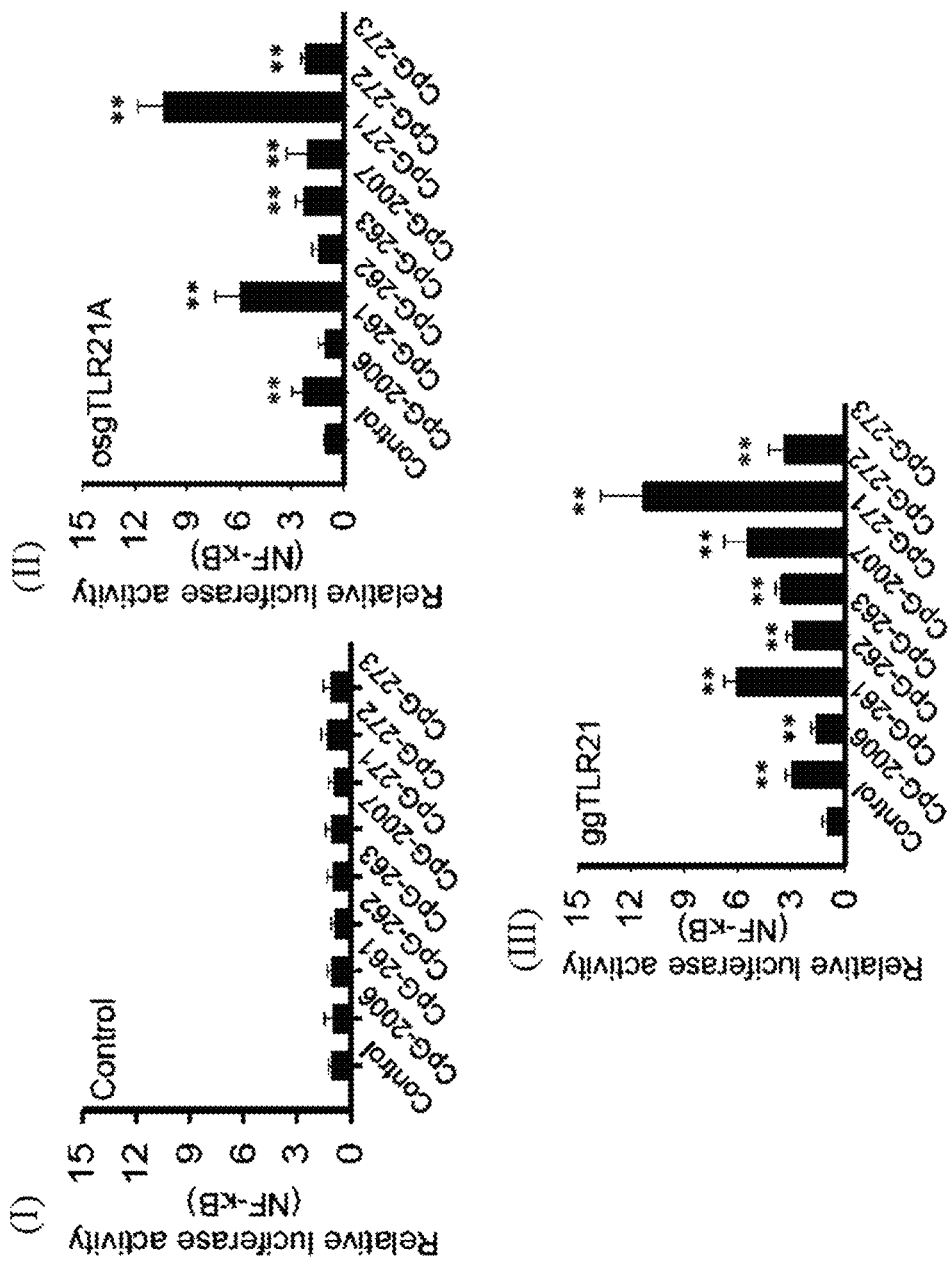

FIG. 4 shows histograms illustrating activation of grouper (*Epinephelus* spp.) TLR21s induced by different types of CpG-ODNs and the trimmed derivatives thereof.

Figure 5:
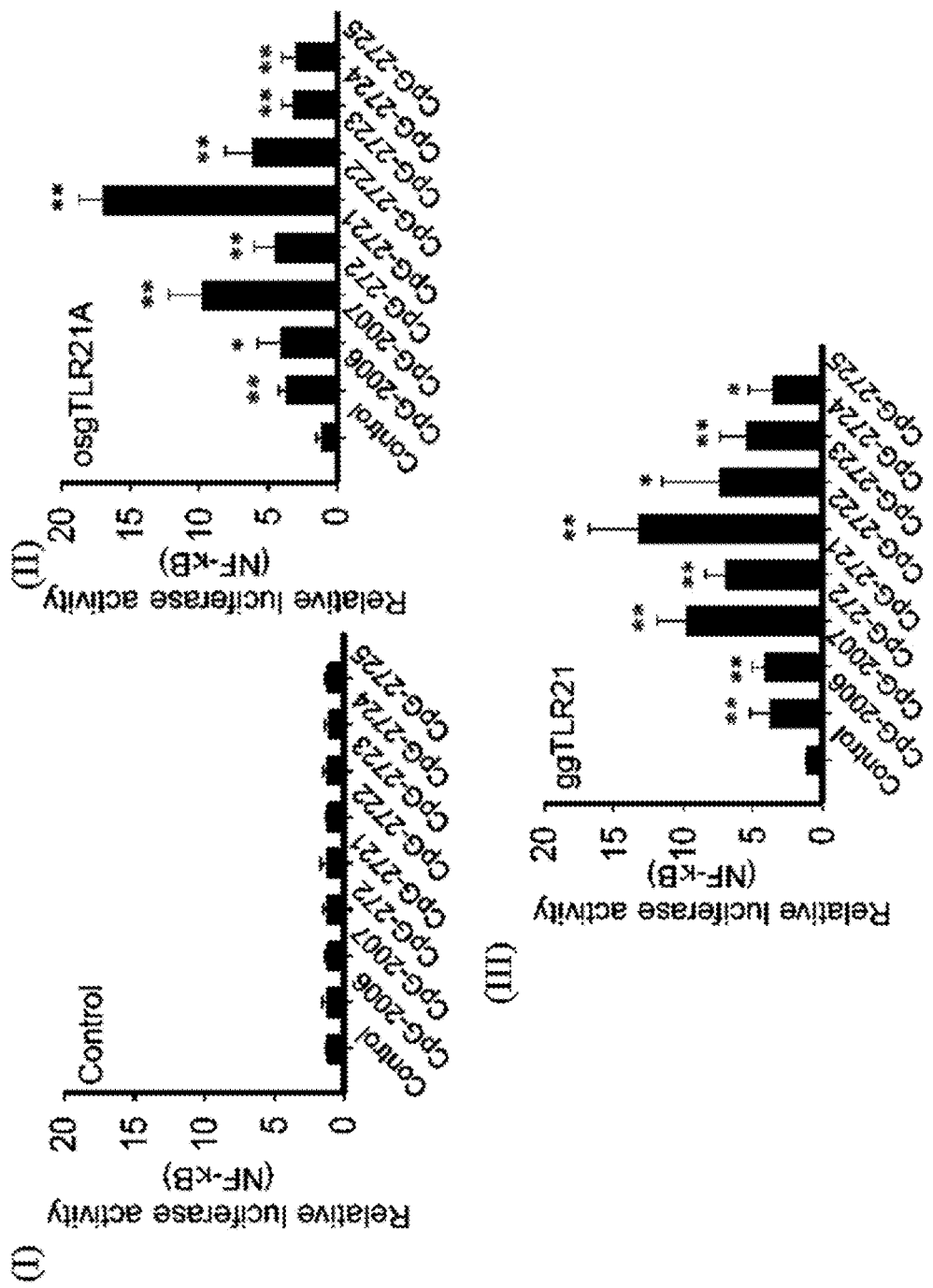

FIG. 5 shows histograms illustrating activation of grouper (*Epinephelus* spp.) TLR21s induced by different types of CpG-ODNs and the trimmed derivatives of the CpG-ODNs in FIG. 3 having higher activities.

Figure 6:
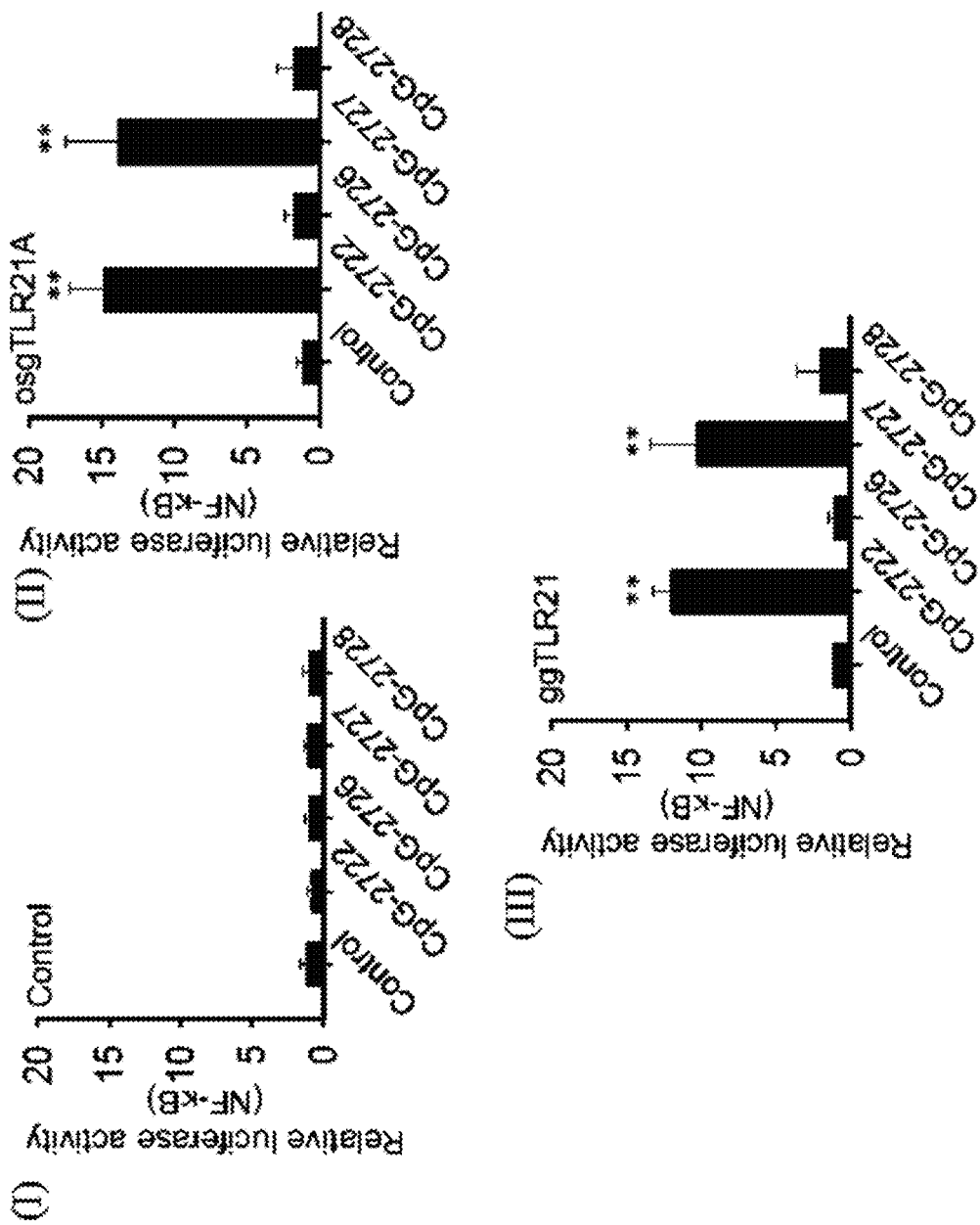

FIG. 6 shows histograms illustrating activation of grouper (*Epinephelus* spp.) TLR21s induced by different types of the trimmed derivatives of the CpG-ODNs in FIG. 3 having higher activities.

Figure 7:
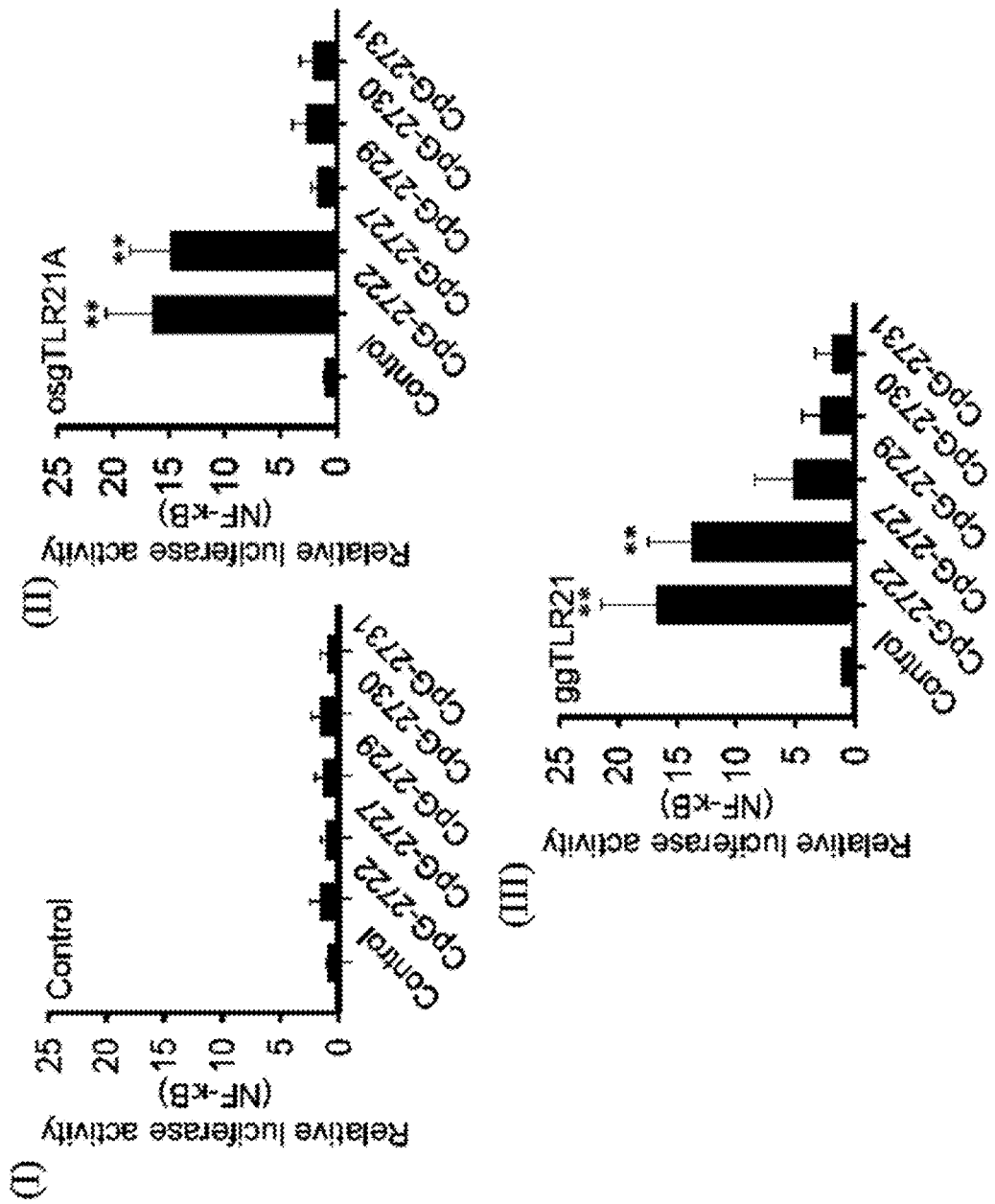

FIG. 7 shows histograms illustrating activation of grouper (*Epinephelus* spp.) TLR21s induced by different types of the trimmed derivatives of the CpG-ODNs in FIG. 3 having higher activities.

Figure 8:
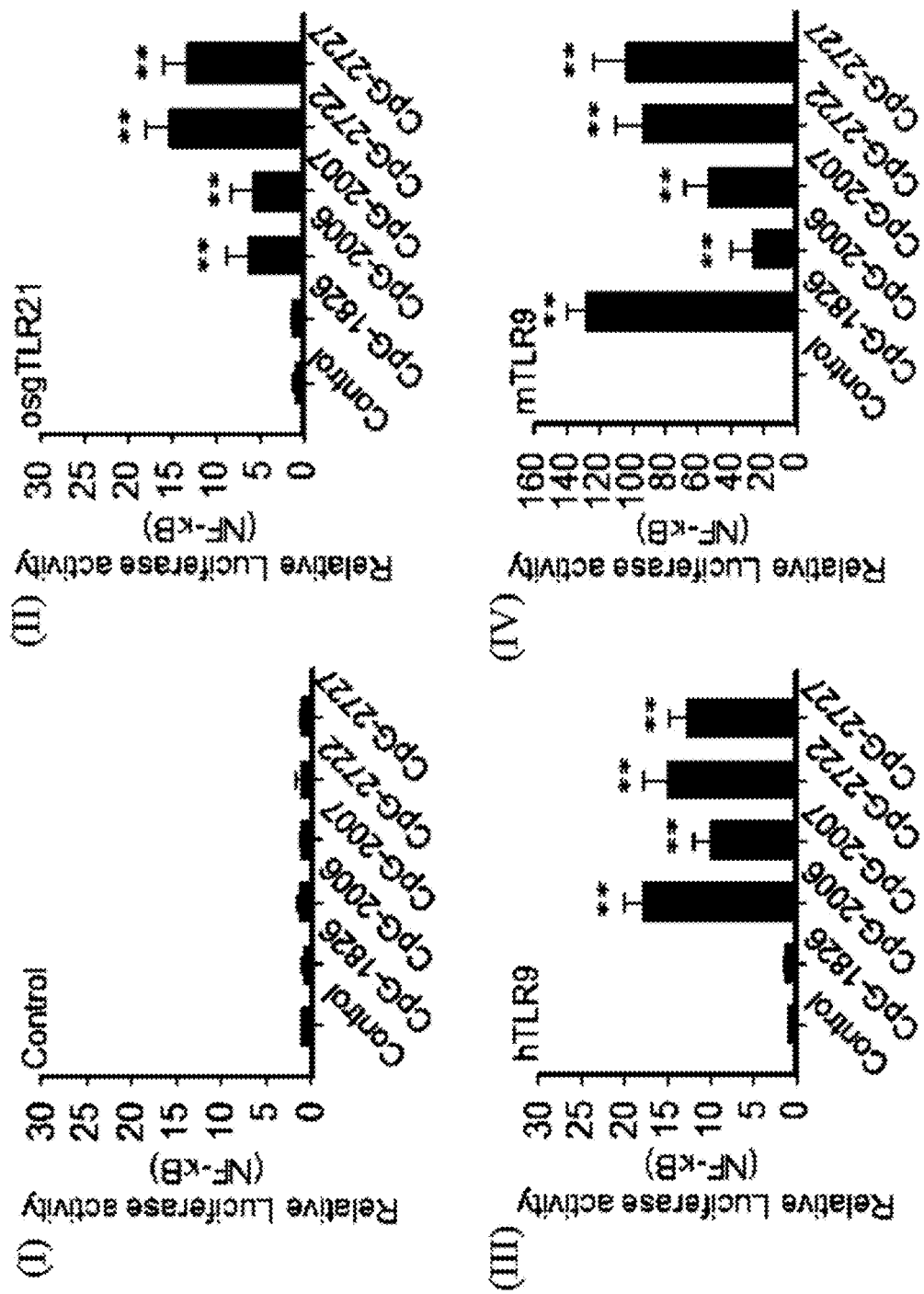

FIG. 8 shows histograms illustrating activation of grouper (*Epinephelus* spp.) TLR21s, human TLR9 and mouse TLR9 induced by different types of CpG-ODNs and the trimmed derivatives thereof.

Figure 9:
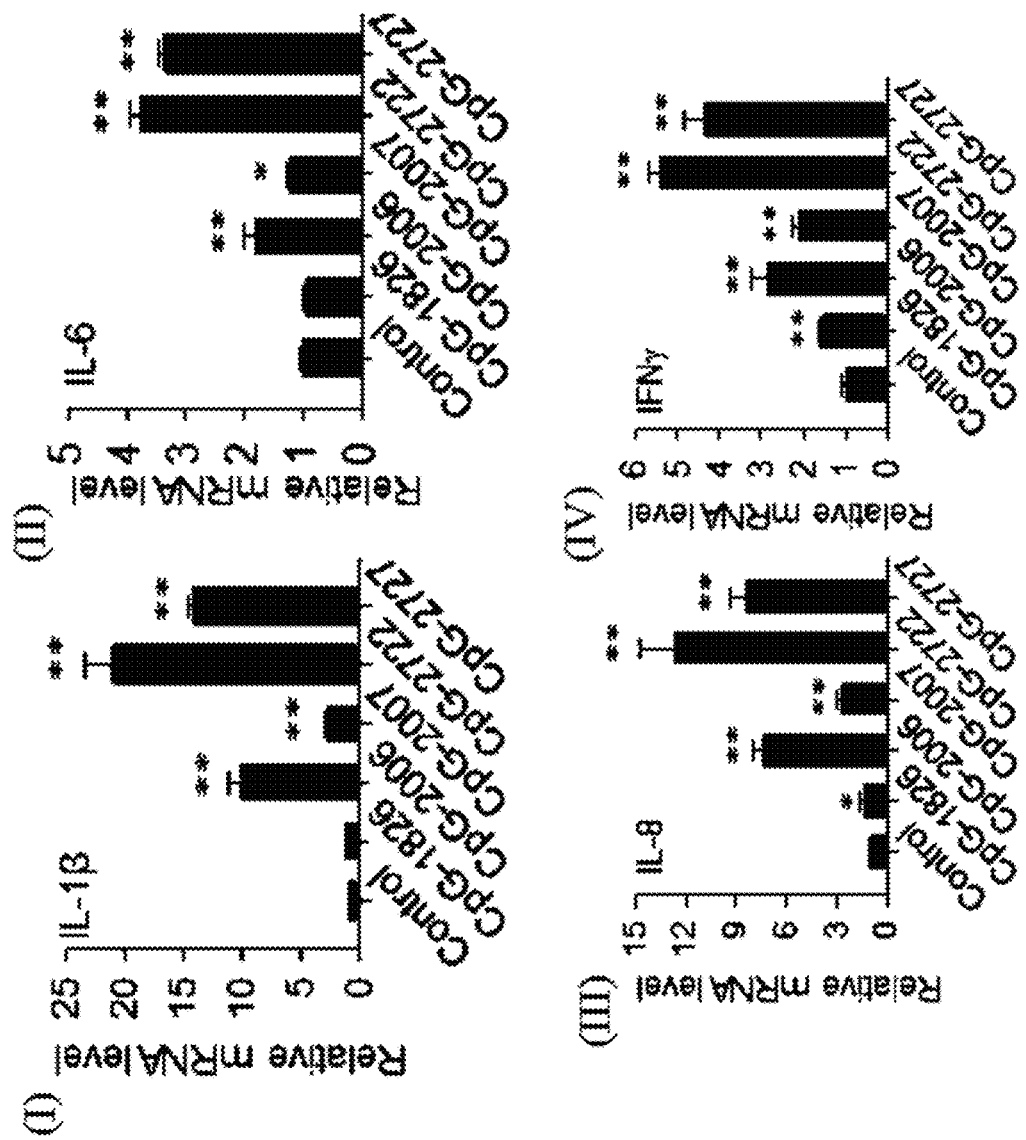

FIG. 9 shows histograms illustrating induction of different kinds of cytokine expression in orange-spotted grouper (*Epinephelus coioides*) head kidney cells by different types of CpG-ODNs and the trimmed derivatives thereof.

Figure 10:
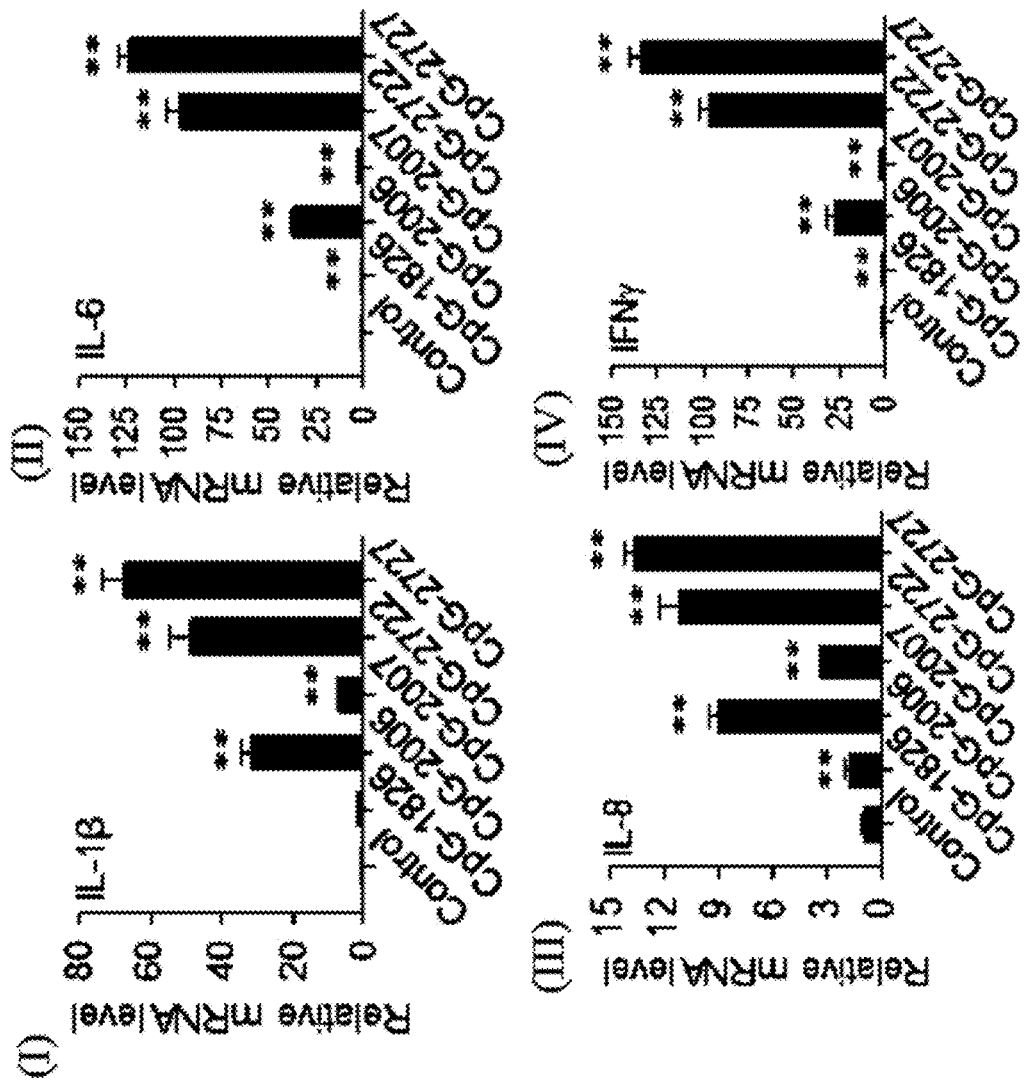

FIG. 10 shows histograms illustrating induction of different kinds of cytokine expression in orange-spotted grouper (*Epinephelus coioides*) splenocytes by different types of CpG-ODNs and the trimmed derivatives thereof.

Figure 11:
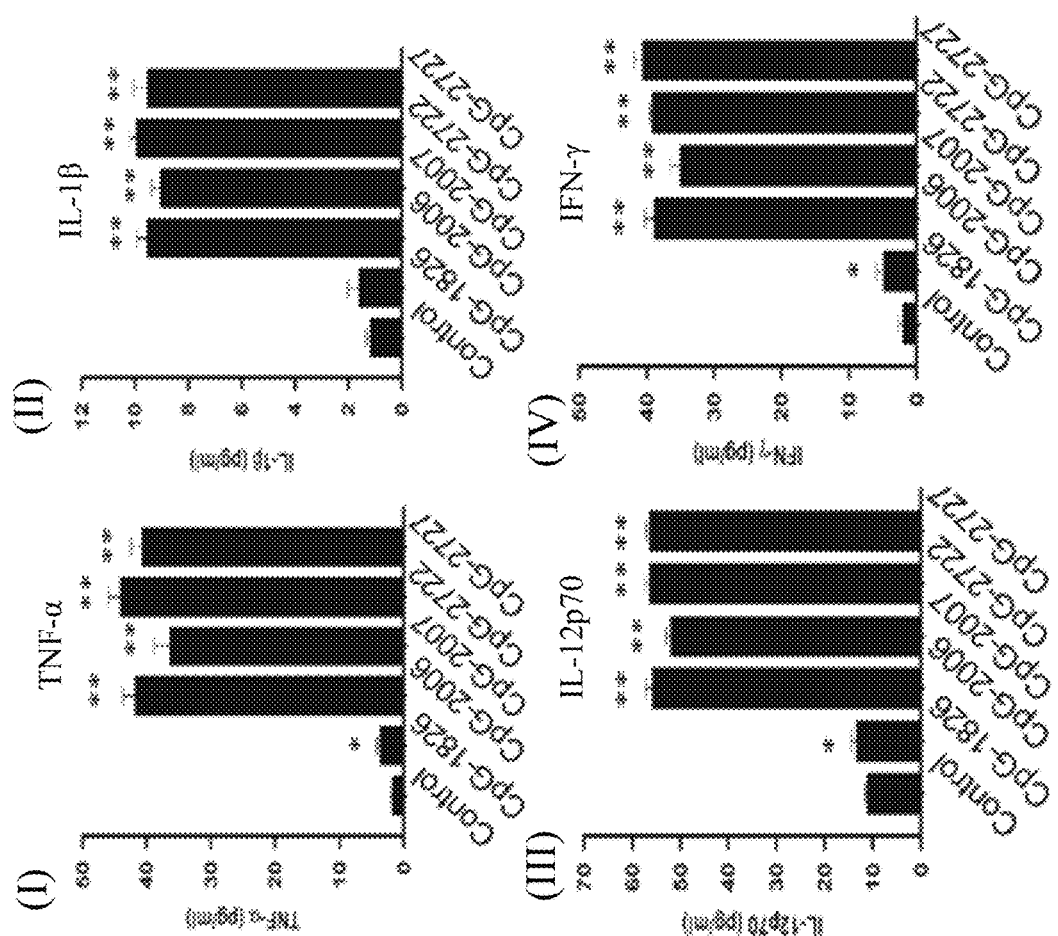

FIG. 11 shows histograms illustrating induction of different kinds of cytokine production in human peripheral blood mononuclear cells (PBMCs) by different types of CpG-ODNs and the trimmed derivatives thereof.

Figure 12:
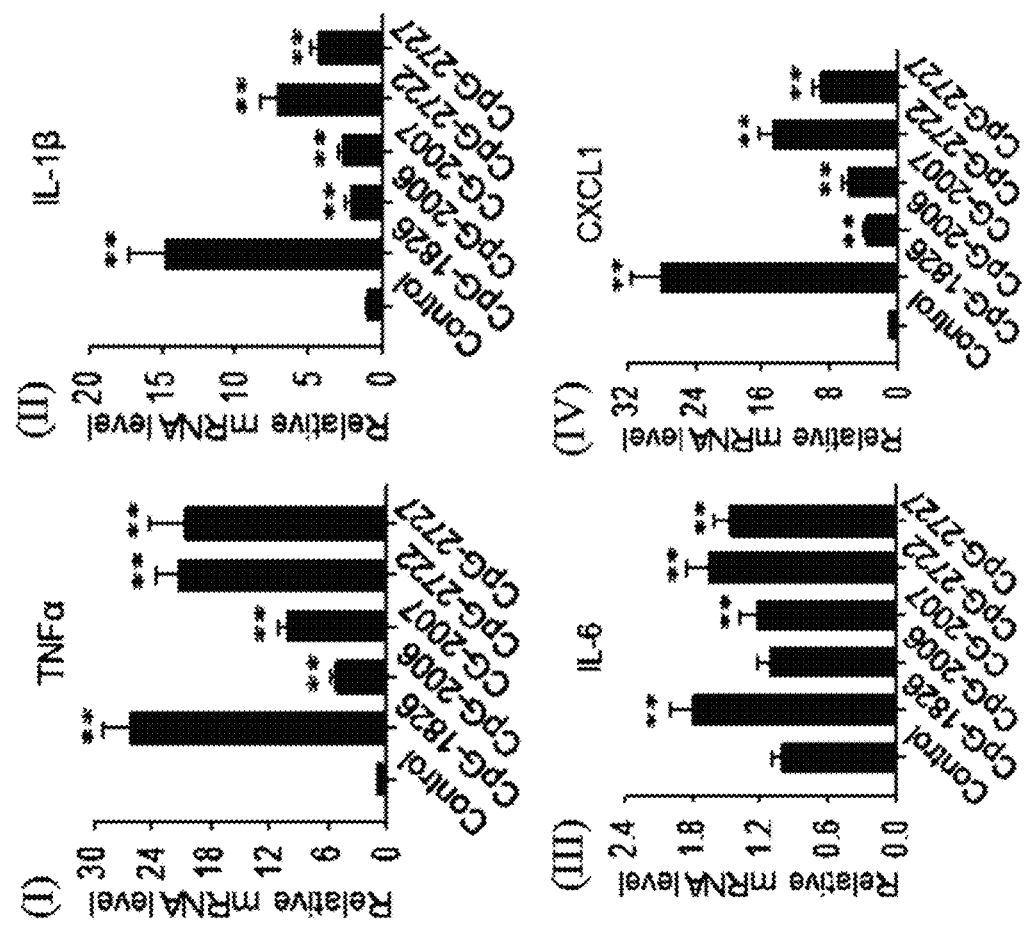

FIG. 12 shows histograms illustrating induction of different kinds of cytokine production in mouse splenocytes by different types of CpG-ODNs and the trimmed derivatives thereof.

Figure 13:
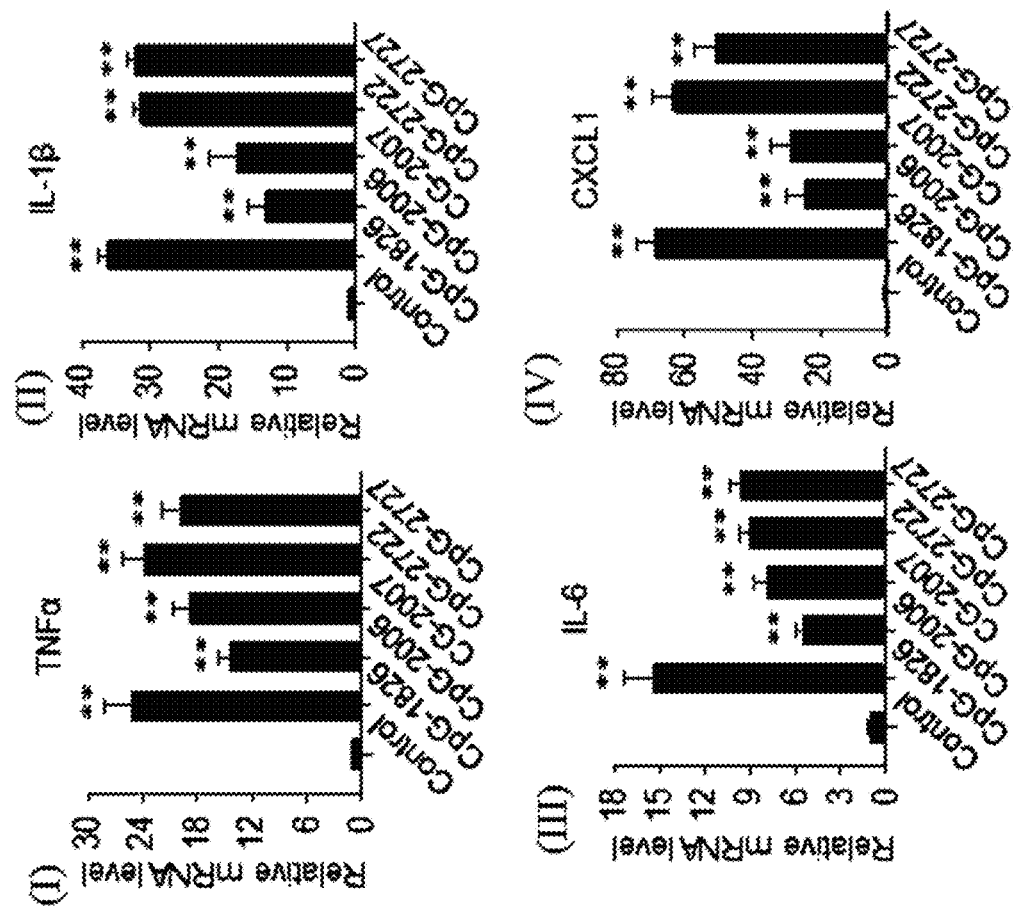

FIG. 13 shows histograms illustrating induction of different kinds of cytokine production in mouse bone marrow-derived macrophages (BMDMs) by different types of CpG-ODNs and the trimmed derivatives thereof.

DESCRIPTION OF THE PREFERRED EMBODIMENTS

For the ease of realizing the technical features, contents, advantages and effects of the present invention by examiners, a detailed description of the embodiments, the appended drawings and tables of the present invention will be stated hereinafter. The drawings are merely used to illustrate and support the content of the specification and are not intended to be limiting in any way regarding the implementation of the present invention that must be explained first.

Methods and procedures of preparing and obtaining materials used in the implementation and used for prove the substantial effects of the present invention will be described below.

In the embodiments of the present invention, head kidney cells and splenocytes of groupers were isolated according to the procedures as follows. Orange-spotted groupers and giant groupers are anesthetized in water containing 0.2 g/L Tricaine, and the head kidneys and spleens thereof are aseptically removed. The organs were then gently minced and passed through a 70-μm strainer with homogenization buffer (standard Hank's balanced salt solution (sHBSS) supplemented with 15 mM HEPES, 10% fetal bovine serum (FBS), 1× Antibiotic-Antimycotic, and 50 U/ml heparin). Subsequently, 1 ml of the homogenized tissue suspension is placed into 8 ml of distilled water and 1 ml of 10× phosphate-buffered saline (PBS). Following the removal of gross debris, the cell suspension was centrifuged and washed with 1×PBS twice. The cell pellet was then resuspended in Leibovitz's L-15 cell culture medium (Gibco, Carlsbad, Calif., USA).

Bone marrow-derived macrophages (BMDMs) and splenocytes of C57BL/6 mice were collected and cultured according to the procedures as follows. In terms of BMDMs, mouse bone marrow cells from mouse tibias and femurs were cultured in complete Dulbecco's Modified Eagle Medium (DMEM) with 30% L929 conditioned medium for 5 days, followed by DMEM medium with 10% FBS. In terms of splenocytes, they were cultured in RPMI1640 medium with 10% FBS after obtained. Furthermore, human peripheral blood mononuclear cells (PBMCs) were cultured in RPMI1640 medium with 10% FBS.

TLR21 cDNA of giant groupers (ggTLR21 cDNA) were molecular cloned by procedures as follows. Total RNAs were purified from grouper splenocytes using TRIzol, and first-strand cDNA libraries were then prepared using the SuperScript® III First-Strand Synthesis System (Invitrogen, Carlsbad, Calif., USA), which is known in prior arts (Yeh D. W. et al. Proceedings of the National Academy of Sciences of the United States of America. 2013; 110(51):20711-6). To clone ggTLR21 cDNA, a pair of forward and reverse primers (5'-GAACAGATTCCTGTACCATGTTCATC-3' (SEQ ID NO: 51) and 5'-GCTTGTATGAATTGTCACACT-GCAC-3' (SEQ ID NO: 52) was designed based on the sequences of the 5'- and 3'-untranslated regions of TLR 21 of orange-spotted groupers (osgTLR21) (GenBank: GU198366.2). A ggTLR21 cDNA containing both of the 5'- and 3'-untranslated regions and the complete coding region was cloned from the prepared giant grouper spleen first-strand cDNA library using polymerase chain reaction (PCR) amplification. Further, the cloned ggTLR21 cDNA sequence is submitted to the GenBank database (accession number: KM024068).

Multiple alignments of the amino acid sequences of the TLR21s were performed using ClustalW2. The structural model of the TLR21 protein was predicted with SWISS MODEL, using TLR13 as a template.

The expression constructs for osgTLR21 s and ggTLR21 were generated through PCR amplification of the corresponding protein-coding regions from the generated first-strand cDNA libraries derived from the orange spotted and giant grouper spleens. The forward and reverse primers based on the 5'- and 3'-end cDNA sequences for the coding region of osgTLR21 (GU198366.2) and ggTLR21 (KM024068) are designed and subcloned the amplified DNA fragments into a PEF6 vector in frame with a FLAG tag at their C-terminal ends. The expression vectors for human and mouse TLR9 were generated following previously described methods (Liu J. Comparative immunology, microbiology and infectious diseases. 2012; 35(5):443-51).

In the embodiments of present invention, TLR21 and TLR9 activation assays are performed according to the procedures as follows. Human embryonic kidney (HEK) 293 cells were grown in DMEM supplemented with 10% FBS. Then, the procedures stated in previous art (Yeh D. W. et al. Proceedings of the National Academy of Sciences of the United States of America. 2013; 110(51):20711-6) were performed. Relative luciferase activities were calculated as the fold change compared with an unstimulated control.

Reverse transcription-quantitative PCR (RT-qPCR) analysis of gene expression was performed according to the procedures as follows. Cells were treated with different CpG-ODNs for 4 h. Then, the total RNA is purified using TRIzol and the transcription is performed using, for instance, the SuperScript III First-Strand Synthesis System (Invitrogen, Carlsbad, Calif., USA). Further, RT-qPCR was carried out using appropriate detection methods or kits, for instance, an ABI PRISM 790 reverse OHT Sequence Detection System and KAPA SYBR® fast qPCR kit (KK4605) for gene expression analysis. The expression of mRNA was normalized to β-actin. as below. In Table 1, the sequences of comparative examples are used for explaining the preparation and for comparing with the CpG-ODN of the examples (SEQ ID NOs: 2-3) of the present invention so as to show difference on their effects. Further, the primer sequences used in RT-qPCR are listed in Tables 2 and 3.

TABLE 1

| CpG-ODN | SEQUENCE |
|---|---|
| Comparative examples | |
| CpG-1826 (SEQ ID NO: 4) | TCCATGACGTTCCTGACGTT |
| CpG-2000 (SEQ ID NO: 5) | TCCATGACGTTCCTGCAGTTCCTGACGTT |
| CpG-HC4040 (SEQ ID NO: 6) | TGACTGTGAACGTTCGAGATGA |
| CpG-2006 (SEQ ID NO: 7) | TCGTCGTTTTGTCGTTTTGTCGTT |
| CpG-261 (SEQ ID NO: 8) | TCGTCGTTTTGTCGTT |
| CpG-262 (SEQ ID NO: 9) | GTTTTGTCGTTTTGTCGTT |
| CpG-263 (SEQ ID NO: 10) | TCGTTTTGTCGTTTG |
| CpG-2007 (SEQ ID NO: 11) | TCGTCGTTGTCGTTTTGTCGTT |
| CpG-271 (SEQ ID NO: 12) | TCGTCGTTGTCGTTTTGT |
| CpG-272 (SEQ ID NO: 13) | GTTGTCGTTTTGTCGTT |
| CpG-273 (SEQ ID NO: 14) | TCGTTGTCGTTTTGT |
| CpG-2721 (SEQ ID NO: 15) | GTTGTCGTTGTCGTT |
| CpG-2723 (SEQ ID NO: 16) | GTGTCGTTTTGTCGTT |
| CpG-2724 (SEQ ID NO: 17) | GTTGTCGTTTTGTC |
| CpG-2725 (SEQ ID NO: 18) | GTTGTCGTTTCC |
| CpG-2726 (SEQ ID NO: 19) | GTTGTGCTTTTTTGTCGTT |
| CpG-2728 (SEQ ID NO: 20) | GTTGTGCTTTTTTGTGCTT |
| CpG-2729 (SEQ ID NO: 21) | GTCGTTTTTTGTCGTT |
| CpG-2730 (SEQ ID NO: 22) | GTTGTCGTTTTTT |
| Examples of embodiments | |
| CpG-2731 (SEQ ID NO: 1) | GTCGTTTTT |
| CpG-2722 (SEQ ID NO: 2) | GTTGTCGTTTTTTGTCGTT |
| CpG-2727 (SEQ ID NO: 3) | GTTGTCGTTTTTTGTGCTT |

TABLE 2

| Grouper primers used in RT-qPCR | |
|---|---|
| β-actin | forward 5'-GACATGGTGCGGTTTCTCTT-3' (SEQ ID NO: 23) |
| | reverse 5'-GCCTCTGCTGTGCTGATGTA-3' (SEQ ID NO: 24) |
| TNF-α | forward 5'-GGATCTGGCGCTACTCAGAC-3' (SEQ ID NO: 25) |
| | reverse 5'-TCCGATAGCTGGTTGGTTTC-3' (SEQ ID NO: 26) |
| IL-1β | forward 5'-GACATGGTGCGGTTTCTCTT-3' (SEQ ID NO: 27) |
| | reverse 5'-GCCTCTGCTGTGCTGATGTA-3' (SEQ ID NO: 28) |
| IL-6 | forward 5'-CCTGAAGGACCTCGACAATC-3' (SEQ ID NO: 29) |
| | reverse 5'-TCCTGACAGCCAGACTTCCT-3' (SEQ ID NO: 30) |
| IL-8 | forward 5'-GAGCTGCACTGTCGCTGTAT-3' (SEQ ID NO: 31) |
| | reverse 5'-TGTTGGCCATGATCCTGTTA-3' (SEQ ID NO: 32) |
| Mx | forward 5'-CCATCTGACGCAACTGAGAA-3' (SEQ ID NO: 33) |
| | reverse 5'-TCCACCTCGCAAACTCTCTT-3' (SEQ ID NO: 34) |
| IFN1 | forward 5'-CTGTGTCCTTCCCGAATCAT-3' (SEQ ID NO: 35) |
| | reverse 5'-TGCACAGTACAGGAGCGAAG-3' (SEQ ID NO: 36) |
| IFN gamma | forward 5'-GACCACCAAGATGGAGGCTA-3' (SEQ ID NO: 37) |
| | reverse 5'-TACCGGTGTTTCCTCAGGTC-3' (SEQ ID NO: 38) |
| CCL4 | forward 5'-GTGGTACTGGCCCAAAGAAA-3' (SEQ ID NO: 39) |
| | reverse 5'-GGCTGAAGGTCTGACACACA-3' (SEQ ID NO: 40) |

TABLE 3

Mouse primers used in RT-qPCR

| | | |
|---|---|---|
| gapdh | forward | 5'-ACCCAGAAGACTGTGGATGG-3' (SEQ ID NO: 41) |
| | reverse | 5'-CACATTGGGGGTAGGAACAC-3' (SEQ ID NO: 42) |
| tnf-α | forward | 5'-GGATCTGGCGCTACTCAGAC-3' (SEQ ID NO: 43) |
| | reverse | 5'-TCCGATAGCTGGTTGGTTTC-3' (SEQ ID NO: 44) |
| il-1β | forward | 5'-CAGGCAGGCAGTATCACTCA-3' (SEQ ID NO: 45) |
| | reverse | 5'-AGCTCATATGGGTCCGACAG-3' (SEQ ID NO: 46) |
| il-6 | forward | 5'-AGTTGCCTTCTTGGGACTGA-3' (SEQ ID NO: 47) |
| | reverse | 5'-TCCACGATTTCCCAGAGAAC-3' (SEQ ID NO: 48) |
| cxcl1 | forward | 5'-GCTGGGATTCACCTCAAGAA-3' (SEQ ID NO: 49) |
| | reverse | 5'-CTTGGGGACACCTTTTAGCA-3' (SEQ ID NO: 50) |

Sodium dodecyl sulfate polyacrylamide gel electrophoresis (SDS-PAGE) and immunoblot analysis are performed according to the procedures as follows. Cells were lysed with lysis buffer (100 mM NaCl, 50 mM Tris-Cl (pH 7.5), 0.5 mM ethylenediaminetetraacetic acid (EDTA), 1% octyl-phenoxypolyethoxyethanol (NP-40)) containing complete protease inhibitor cocktail (Roche Life Science, Indianapolis, Ind., USA). Then, cell lysates were separated by SDS-PAGE and transferred onto polyvinylidene fluoride (PVDF) membranes. Subsequently, membranes were incubated with the indicated antibody and then with horseradish peroxidase (HRP)-conjugated secondary antibody of which the immunoreactive bands were visualized using chemiluminescent HRP substrate (Immobilon Western; Millipore, Temecula, Calif., USA) and the UVP BioSpectrum Imaging System.

Human cytokine production results were measured by the procedures as follows. PBMCs were treated with different CpG-ODNs for 24 h, and then the culture supernatant is collected for cytokine measurement. The production of tumor necrosis factor (TNF)-α, interleukin (IL)-1β, IL-12p70, and interferon (IFN)-γ were measured using ELISA Kits.

Furthermore, all of the results shown in the present disclosure are expressed as the mean±SD of three independent experiments. Statistical analyses were performed using Student's t-test with a significance level of $P<0.05$.

Here, several embodiments will be described with the results and the appended drawings for of the present invention for ease of realizing the effects of the CpG-ODNs provided by the present invention.

In an embodiment of the present invention, ggTLR21 may be cloned according to the methods mentioned above. The cDNA from osgTLR21A and osgTLR21B may be cloned according to the previous publication (Li Y. W. et al. Cryptocaryon irritans infection. Fish & shellfish immunology. 2012; 32(3):476-81). The main difference between their encoded protein sequences is the absence of four amino acid residues at the C-terminal end of osgTLR21B, as shown in FIGS. 1B-1F. Based on the expected high identity between nucleotide sequences of the same gene in giant grouper and orange-spotted grouper, the inventor designs two primers based on the 5'- and 3'-untranslated regions of osgTLR21 to clone ggTLR21. This results in a full-length ggTLR21 cDNA which is homologous to osgTLR21A but not osgTLR21B.

Then, the characteristics of the grouper TLR21s used in the present invention may be analyzed. To compare the grouper TLR21s with other TLRs, the inventor aligns their protein sequences with those of different zebrafish TLRs using ClustalW2 and constructed an evolution tree as shown in FIG. 2A, wherein the proteins sequences and labels thereof are obtained from the GenBank database. As results, the protein identity was 98.26% between ggTLR21 and osgTLR21A, 98.15% between ggTLR21 and osgTLR21B, 54.44% between zebrafish (zeb) TLR21 and ggTLR21, and 28.30% between zebTLR22 and ggTLR21A. TLR22 was closest to TLR21 in the evolution tree, with TLR13 and TLR20f the next closest.

Further, as shown in FIG. 2B, phylogenetic analysis using the protein sequences of TLR21s from different fish and avian species show that the grouper TLR21s were most closely related to *Oplegnathus fasciatus* TLR21, followed by *Paralichthys olivaceus* and *Scophthalmus maximus* TLR21s, and were more distantly related to chicken (*Gullas gullas*), duck (*Anas platyrhynchos*), and goose (*Anser cygnoides*) TLR21s.

On the other hand, the sequences and structures of TLR21s between difference species of groupers may be also analyzed. As results, ggTLR21 contains 979 amino acid residues, while osgTLR21A and osgTLR21B contain 979 and 975, respectively. Alignment of these three protein sequences shows that they contain an extracellular domain (ectodomain), a transmembrane domain, and a Toll/IL-1 (TIR) cytosolic domain. They also have 23 copies of leucine-rich repeats (LRRs) and a C-terminal leucine-rich repeat (LRR-CT) in their ectodomain. Only 14 of 741 amino acid residues are differed between the ectodomain of osgTLR21 and ggTLR21. Several three-dimensional structures of different TLR ectodomains have been resolved in prior arts, of which TLR13 is phylogenetically closest to TLR21. Therefore, the inventor predicts the three-dimensional structures of the osgTLR21 and ggTLR21 ectodomains with SWISS MODEL software using TLR13 as a template to further examine their difference. This shows that their ectodomains are relatively similar to horseshoe-shaped solenoid three-dimensional structures, except for the extrusion of a small helix structure at the 315-330 amino acid regions in osgTLR21, as shown in FIG. 1A in which from left to right is the result of predicted ectodomain structure of osgTLR21 (black), ggTLR21 (white), and superimposition (black: osgTLR21; white: ggTLR21) of these two ectodomains. (N: N-terminal end, C: C-terminal end of the ectodomain). Referring to FIGS. 1B-1F, the three motifs boxes 1-3 that are required for signal transduction of mammalian TLRs are conserved in the TIR domains of all three grouper TLR21s. However, osgTLR21B differs from osgTLR21A and ggTLR21 in that it lacks a four amino acid residue region at the C-terminal end after box 3 (Asterisk, identical residues; single dot, conservative substitutions; two dots, highly conservative substitutions).

Subsequently, to investigate whether the structural differences between these grouper TLR21 s translates into differences in their activity in response to different types of CpG-ODNs stimulation, the inventor co-transfects HEK293 cells with the expression vector for these TLR21s and the nuclear factor (NF)-κB controlled luciferase reporter gene to establish a cell-based activation assay. Then, the inventor treats these cells with CpG-ODNs with different hexamer motifs and sequences, as shown in Table 1, and measures the induced luciferase reporter activities. As shown in parts (I) to (IV) of FIG. 3, it was found that osgTLR21A, osgTLR21B, and ggTLR21 experience the same level of activation by CpG-ODNs containing GTCGTT hexamer motifs (i.e., CpG-2006 [SEQ ID NO: 7] and CpG-2007), but do not respond to CpG-ODNs containing GACGTT and AACGTT hexamer motifs (i.e., CpG-1826, CpG-2000 [SEQ ID NO: 5], and CpG-HC4040 [SEQ ID NO: 6]). The results suggest that all three grouper TLRs are functional and these minor structural differences do not significantly affect their response to CpG-ODN stimulation.

According to the above results, in an attempt to develop CpG-ODNs for strong activation of grouper TLR21s, the inventor trims the length of CpG-2006 and CpG-2007 to retain only the left or right two of the three GTCGTT hexamer motifs to generate CpG-261 (SEQ ID NO: 8) and CpG-271 (SEQ ID NO: 12), and CpG-262 (SEQ ID NO: 9) and CpG-272 (SEQ ID NO: 13), respectively. Further, the inventor also trims their length to retain only the middle copy (Table 1). Then, the activities of these CpG-ODNs are determined by an osgTLR21 and ggTLR21 cell-based activation assay and being compared with CpG-2006 and CpG-2007. As results shown in parts (I) to (III) of FIG. 4, it was found that CpG-272 has the best activities toward the osgTLR21 s and ggTLR21 of the hexamer motif to generate CpG-263 (SEQ ID NO: 10) and CpG-273 (SEQ ID NO: 14). Therefore, inventor further hexamer motifs to generate CpG-2721 (SEQ ID NO: 15), CpG-2722 (SEQ ID NO: 2), CpG-2723 (SEQ ID NOs: 16), CpG-2724 (SEQ ID NO: 17) and CpG-2725 (SEQ ID NO: 18) (Table 1). A further cell-based assay was performed and the results indicate that CpG-2722 has the best activity toward the osgTLR21 s and ggTLR21, as shown in part (I) to (III) of FIG. 5.

Since the CpG-hexamer motifs activating the grouper TLR21s were found in above results, the inventor further investigates whether the number of CpG-hexamer motifs and structure of the CpG-2722 influence the activation of grouper TLR21s. In the above results, CpG-2722 which contains two copies of the GTCGTT hexamer motif in a length of nineteen nucleotides has the best activity. To determine whether both copies are required for its activity, the inventor reverses the CpG-dideoxynucleotides in its 5'- and 3'-CpG-hexamer motif to generate CpG-2726 (SEQ ID NO: 19), CpG-2727 (SEQ ID NO: 3) and CpG-2728 (SEQ ID NO: 20) (Table 1). As the results shown in part (I) to (III) of FIG. 6 activation assays of from osgTLR21 and ggTLR21 indicated that the activity of CpG-2727 is as good as that of CpG-2722, whereas CpG-2726 and CpG-2728 were unable to activate the osgTLR21s and ggTLR21 grouper TLR21s. These findings suggest that only one copy of the 5'-CpG-hexamer motif is required for CpG-2722 activity. The CpG-2722 was further trimmed to generate CpG-2729 (SEQ ID NO: 21) by removing three nucleotides from 5'-end, CpG-2730 (SEQ ID NO: 22) by removing the 3'-CpG-hexamer motif, and CpG-2731 (SEQ ID NO: 1) by removing both of the three nucleotides from 5'-end and the 3'-CpG-hexamer motif (Table 1).

Furthermore, the activities of these CpG-ODNs were tested and the results are shown as in parts (I) to (III) of FIG. 7. The results showed that the three 5'-end nucleotides were required for the CpG-2722 to strongly active both of the osgTLR21 and ggTLR21, and although the 3'-CpG-hexamer motif is not required for the activity of CpG-2722, these nucleotides are required to maintain the nineteen nucleotide length of CpG-2722 for its activity.

Additionally, as shown in parts (I) to (IV) of FIG. 8, the inventor tests the activities of CpG-2722 and CpG-2727 on human (h) and mouse (m) TLR9s to determine whether they are specific to grouper TLR21s. Interestingly, in the hTLR9 activation assay, according to the results, it was found that the activities of CpG-2722 and CpG-2727 were as good as those of CpG-2006 and CpG-2007, which have been optimized for the activation of human cells. Furthermore, in the mTLR9 activation assay, although the activities of CpG-2722 and CpG-2727 were not as good as that of CpG-1826, which has been optimized for the activation of mouse cells, both had better activities toward mTLR9 than CpG-2006 and CpG-2007.

Further, the inventor investigates the effects of CpG-2722 and CpG-2727 on the induction of cytokine productions in grouper, human, and mouse cells to compare their activities on these cells with that showed on the cell-based activation assays in parts (I) to (IV) of FIG. 8. Head kidney cells and splenocytes are purified from orange-spotted groupers, treated with different CpG-ODNs for determining the induction of the cytokines IL-1α, IL-6, IL-8, and IFNγ. In consistent with results obtained from the cell based assays as show in parts (I) to (IV) of FIG. 9 and parts (I) to (IV) of FIG. 10, it was found that CpG-2722 and CpG-2727 have greater effects on the activation of cytokine production in orange-spotted grouper cells than CpG-1826, CpG-2006, and CpG-2007. In addition, an ELISA analysis is also performed to show that CpG-2722 and CpG-2727 are as potent as CpG-2006 and CpG-2007 in inducing cytokine production in human PBMCs, whereas CpG-1826 had weak activity on these cells, as shown in parts (I) to (IV) of FIG. 11. Furthermore, CpG-2722 and CpG-2727 were found more potent than the CpG-2006 and 2007 in inducing cytokine expression in mouse splenocytes and BMDMs as the results shown in parts (I) to (IV) of FIG. 12 and parts (I) to (IV) of FIG. 13. These findings suggest that CpG-2722 and CpG-2727, which were developed for grouper TLR21s, also effectively activate immune responses in human and mouse cells.

According to the embodiments and results stated above, more details of the present invention may be described and explained in following paragraphs.

Generally, TLR9 and TLR21 are the cellular receptors for CpG-ODNs. TLR9 is expressed in both mammalian and fish species, and has been better studied in terms of the structural requirements for CpG-ODN to strongly and species-specifically activate this TLR. CpG-ODNs that have been optimized for humans are currently being investigated for their application as vaccine adjuvants, as well as is immunotherapies for allergies, infectious diseases, and cancers. Similarly, CpG-ODNs have also been shown to exert potent immunostimulatory activities in chicken, duck, and fish, which contain TLR21 in previous arts, suggesting potential veterinary uses of CpG-ODNs as immune modulators and vaccine adjuvants. However, few studies have investigated the structural requirements for CpG-ODN to activate TLR21, and it remains unclear whether there is a common structure that will activate both TLR9 and TLR21. Therefore, in the present invention, the inventor develops CpG-ODNs for strong activation of TLR21s in grouper, which are considered an important aquaculture species in Asia due to their rapid growth and good price, and investigated the interaction between CpG-ODNs, grouper TLR21s, and human and mouse TLR9s.

The inventor found that CpG-ODNs that contained the GTCGTT motif, such as CpG-2006 and CpG-2007, may activates grouper TLR21s, whereas those that contained the GACGTT and AACGTT motifs, such as CpG-1826, CpG-2000, and HC4040, does not. Similarly, it has previously been shown that zebTLR9s broadly recognize CpG-ODNs with different CpG-hexamer motifs, with those containing the GACGTT or AACGTT motifs having better activity toward TLR9, and with the GTCGTT motif having better activity toward zebTLR21 (Yeh D. W. et al. Proceedings of the National Academy of Sciences of the United States of America. 2013; 110(51):20711-6). Thus, the grouper TLR21s have a similar CpG-hexamer recognition profile to zebTLR21.

In the present invention, two CpG-ODNs that have better activities toward grouper TLR21s than CpG-2006 and CpG-2007 are provided. CpG-2722 has a length of 19 deoxynucleotides and contains two GTCGTT motifs with four spacing nucleotides between them, while CpG-2727 is a modification of CpG-2722 in which the CpG-dideoxynucleotides in the GTCGTT motif has been reversed. Therefore, the good activity of CpG-2722 suggests that one copy of the GTCGTT motif is sufficient for strong activation of grouper TLR21s. In a previous study that developed CpG-ODNs that strongly activate rabbit TLR9, it was found that the length of a CpG-ODN also affects its activity (Chuang T H, et al. PloS one. 2014; 9(9):e108808). Thus, the fact that CpG-2722 and CpG-2727 contain the same type of CpG-hexamer as CpG-2006 and CpG-2007, but have different lengths and numbers of the CpG hexamer suggests that the key structural elements for designing CpG-ODNs to strongly activate TLR21 are the same as those for TLR9.

In the embodiments and results stated above, the activities of CpG-2722 and CpG-2727 in cells isolated from the head kidneys and spleens of orange-spotted groupers, which should contain both TLR9 and TLR21, are also investigated. This shows that although the activation profile is not entirely the same as for grouper TLR21s, CpG-2722 and CpG-2727 exhibits a greater effect on cytokine production in these cells than CpG-2006, CpG-2007, and CpG-1826. Thus, the CpG-2722 and CpG-2727 may also have good activity toward grouper TLR9, and it appears that both TLR9 and TLR21 cooperatively mediate the immunostimulatory activities of CpG-ODNs in groupers, as previously demonstrated for zebTLR9 and zebTLR21 by CpG-ODNs with the GTCGTT motif (Yeh D. W. et al. Proceedings of the National Academy of Sciences of the United States of America. 2013; 110(51): 20711-6). Alternatively, this may suggest that TLR21 is the major receptor for CpG-ODNs in grouper cells.

On other hand, human and mouse TLR9s have been shown to have species-specific ligand recognition properties, with human TLR9 being strongly activated by CpG-2006 and CpG-2007, but weakly activated by CpG-1826, and mouse TLR9 being preferentially activated by CpG-1826. Here, the inventor found that the activities of CpG-2722 and CpG-2727 were as strong as those of CpG-2006 and CpG-2007 in terms of the activation of human TLR9 and cytokine production in human PBMCs. Furthermore, these two CpG-ODNs also have better effects than CpG-2006 and CpG-2007 on the activation of mouse TLR9 and cytokine production in mouse cells. This suggests that the structures of these two developed CpG-ODNs can better override the specific-specific ligand recognition properties of human and mouse TLR9s, and also share a common structure for the activation of TLR9s and TLR21s from different species. Thus, these two CpG-ODNs may have potential for use as immunomodulatory or vaccine adjuvants in a range of species.

In summary, the present invention provides CpG-ODNs for inducing a TLR9 activated immune response, a TLR21 activated immune response or a combination thereof in a host, wherein the CpG-ODNs comprises one or more copies of the sequence of GTCGTT, one or more copies of the sequence of GTT and one or more copies of the sequence of TTTT. Further, at least one copy of the sequence of GTCGTT is encoded between the sequence of GTT and the sequence of TTTT. Preferably, the sequence of TTTT may be encoded right after the GTCGTT, that is, may be the sequence of GTCGTTTTTT (SEQ ID NO: 1).

Preferably, the CpG-ODNs having better activities toward TLR9 and TLR21 are CpG-2722 (SEQ ID NO: 2) and CpG-2727 (SEQ ID NO: 3) which show better efficiencies in the results described above.

The host of which the immune responses is being to be activated by the CpG-ODNs provided by the present invention may be species expressing TLR9 and/or TLR21 such as human, ayes, rodent and pisces or any other appropriate species.

Also, the CpG-ODNs of the present invention may be combined with a vehicle, and/or an excipient or any other pharmaceutically acceptable additives as an immunogenic composition to improve the practicality or biocompatibility thereof. Preferably, the immunogenic composition may also be combined with an antigen to achieve the improvement of the treatment, specific targeting, or any other additional functions. Preferably, the antigen may be HBsAg, listeriolysin O, apical membrane antigen 1, MART1, and leishmanial.

The CpG-ODNs and the immunogenic compositions of the present invention may also be used in a method of activating an immune response of a host. The method may comprise steps of preparing an effective dose of the CpG-ODN or an immunogenic compositions containing effective dose of the CpG-ODN and administrating the prepared products into a host.

In the method of activating an immune response of a host of the present invention, the effective dose may preferably be 0.01 mg/kg to 20 mg/kg, more preferably 0.1 mg/kg to 20 mg/kg, 0.2 mg/kg to 10 mg/kg, 0.5 mg/kg to 5 mg/kg.

Preferably, the host of the present invention may be a living subject under a demand of a treatment or prevention of a disorder comprising a cancer, such as breast, prostate, melanoma, lymphoma, non-small-cell lung cancer, basal cell carcinoma, glioblastoma, and ovarian cancer and an infectious disease such as induced by hepatitis B virus, B. anthrax, malaria, S. pneumoniae, herpes simplex virus, and influenza virus.

Further, in the method of the present invention, the administrating may be administrating orally, by means of an injection or any other general administration methods.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A CpG-oligodeoxynucleotide (CpG-ODN) for inducing a TLR9 activated immune response, a TLR21 activated immune response or a combination thereof in a host, comprising:
   one or more copies of the sequence of GTCGTT;
   one or more copies of the sequence of GTT; and
   one or more copies of the sequence of TTTT;
   wherein at least one copy of the sequence of GTCGTT is encoded between the sequence of GTT and the sequence of TTTT, and
   the CpG-ODN comprises the sequence of SEQ ID NO: 1.

2. A CpG-oligodeoxynucleotide (CpG-ODN) for inducing a TLR9 activated immune response, a TLR21 activated immune response or a combination thereof in a host, comprising:
   one or more copies of the sequence of GTCGTT;
   one or more copies of the sequence of GTT; and
   one or more copies of the sequence of TTTT;
   wherein at least one copy of the sequence of GTCGTT is encoded between the sequence of GTT and the sequence of TTTT, and the CpG-ODN has having a length of 19 nucleotides.

3. A CpG-oligodeoxynucleotide (CpG-ODN) for inducing a TLR9 activated immune response, a TLR21 activated immune response or a combination thereof in a host, comprising:
   one or more copies of the sequence of GTCGTT;
   one or more copies of the sequence of GTT; and
   one or more copies of the sequence of TTTT;
   wherein at least one copy of the sequence of GTCGTT is encoded between the sequence of GTT and the sequence of TTTT, and the CpG-ODN comprises the sequence of SEQ ID NO: 2 or SEQ ID NO: 3.

4. The CpG-ODN as in claim 1, wherein the host is selected from the group consisting of human, ayes, rodent and pisces.

5. An immunogenic composition for inducing a TLR9 activated immune response, a TLR21 activated immune response or a combination thereof, comprising:
   the CpG-ODN as in claim 1;
   and
   a vehicle, an excipient or a combination thereof.

6. The immunogenic composition as in claim 5, further comprising an antigen selected from the group consisting of: virus, bacterium, protozoa, and tumor.

7. A method of inducing an immune response of a host for treating or preventing a disorder, comprising:
   preparing an immunogenic composition for inducing a TLR9 activated immune response, a TLR21 activated immune response or a combination thereof, including an effective dose of a CpG-ODN, wherein the CpG-ODN is as in claim 1;
   and
   administrating the immunogenic composition to the host.

8. The method as in claim 7, wherein the host is selected from the group consisting of human, ayes, rodent and pisces.

9. The method as in claim 7, wherein the effective dose is 0.01 mg/kg body weight to 20 mg/kg body weight.

10. The method as in claim 7, wherein the disorder is selected from the group consisting of breast cancer, prostate cancer, melanoma, lymphoma, non-small-cell lung cancer, basal cell carcinoma, glioblastoma, ovarian cancer, and an infectious disease induced by hepatitis B virus, B. anthrax, malaria, *S. pneumoniae*, herpes simplex virus, influenza virus or a combination thereof.

11. The method as in claim 7, wherein the administrating comprises administrating orally or by means of injection.

12. An immunogenic composition for inducing a TLR9 activated immune response, a TLR21 activated immune response or a combination thereof, comprising:
    the CpG-ODN as in claim 2; and
    a vehicle, an excipient or a combination thereof.

13. An immunogenic composition for inducing a TLR9 activated immune response, a TLR21 activated immune response or a combination thereof, comprising:
    the CpG-ODN as in claim 3; and
    a vehicle, an excipient or a combination thereof.

14. A method of inducing an immune response of a host for treating or preventing a disorder, comprising:
    preparing an immunogenic composition for inducing a TLR9 activated immune response, a TLR21 activated immune response or a combination thereof, including an effective dose of a CpG-ODN, wherein the CpG-ODN is as in claim 2; and
    administrating the immunogenic composition to the host.

15. A method of inducing an immune response of a host for treating or preventing a disorder, comprising:
    preparing an immunogenic composition for inducing a TLR9 activated immune response, a TLR21 activated immune response or a combination thereof, including an effective dose of a CpG-ODN, wherein the CpG-ODN is as in claim 3; and
    administrating the immunogenic composition to the host.

* * * * *

SEQUENCE LISTING

<160> NUMBER OF SEQ ID NOS: 52

<210> SEQ ID NO 1
<211> LENGTH: 10
<212> TYPE: DNA
<213> ORGANISM: Artificial Sequence
<220> FEATURE:
<223> OTHER INFORMATION: An aspect of the CpG-ODN of the present
      invention.

<400> SEQUENCE: 1
gtcgttttt                                                              10

<210> SEQ ID NO 2
<211> LENGTH: 19
<212> TYPE: DNA
<213> ORGANISM: Artificial Sequence
<220> FEATURE:
<223> OTHER INFORMATION: An aspect of the CpG-ODN of the present
      invention.

<400> SEQUENCE: 2
gttgtcgttt tttgtcgtt                                                   19

<210> SEQ ID NO 3
<211> LENGTH: 19
<212> TYPE: DNA
<213> ORGANISM: Artificial Sequence
<220> FEATURE:
<223> OTHER INFORMATION: An aspect of the CpG-ODN of the present
      invention

<400> SEQUENCE: 3
gttgtcgttt tttgtgctt                                                   19

<210> SEQ ID NO 4
<211> LENGTH: 20
<212> TYPE: DNA
<213> ORGANISM: Artificial Sequence
<220> FEATURE:
<223> OTHER INFORMATION: CpG-1826, a comparative example of the present
      invention.

<400> SEQUENCE: 4
tccatgacgt tcctgacgtt                                                  20

<210> SEQ ID NO 5
<211> LENGTH: 29
<212> TYPE: DNA
<213> ORGANISM: Artificial Sequence
<220> FEATURE:
<223> OTHER INFORMATION: CpG-2000, a comparative example of the present
      invention.

<400> SEQUENCE: 5
tccatgacgt tcctgcagtt cctgacgtt                                        29

<210> SEQ ID NO 6
<211> LENGTH: 22
<212> TYPE: DNA
<213> ORGANISM: Artificial Sequence
<220> FEATURE:
<223> OTHER INFORMATION: CpG-HC4040, a comparative example of the
      present invention.

<400> SEQUENCE: 6
tgactgtgaa cgttcgagat ga                                               22

<210> SEQ ID NO 7
<211> LENGTH: 24
<212> TYPE: DNA
<213> ORGANISM: Artificial Sequence
<220> FEATURE:
<223> OTHER INFORMATION: CpG-2006, a comparative example of the present
      invention.

<400> SEQUENCE: 7
tcgtcgtttt gtcgttttgt cgtt                                          24

<210> SEQ ID NO 8
<211> LENGTH: 16
<212> TYPE: DNA
<213> ORGANISM: Artificial Sequence
<220> FEATURE:
<223> OTHER INFORMATION: CpG-261, a comparative example of the present
      invention.

<400> SEQUENCE: 8
tcgtcgtttt gtcgtt                                                   16

<210> SEQ ID NO 9
<211> LENGTH: 19
<212> TYPE: DNA
<213> ORGANISM: Artificial Sequence
<220> FEATURE:
<223> OTHER INFORMATION: CpG-262, a comparative example of the present
      invention.

<400> SEQUENCE: 9
gttttgtcgt tttgtcgtt                                                19

<210> SEQ ID NO 10
<211> LENGTH: 16
<212> TYPE: DNA
<213> ORGANISM: Artificial Sequence
<220> FEATURE:
<223> OTHER INFORMATION: CpG-263, a comparative example of the present
      invention.

<400> SEQUENCE: 10
tcgttttgtc gttttg                                                   16

<210> SEQ ID NO 11
<211> LENGTH: 22
<212> TYPE: DNA
<213> ORGANISM: Artificial Sequence
<220> FEATURE:
<223> OTHER INFORMATION: CpG-2007, a comparative example of the present
      invention.

<400> SEQUENCE: 11
tcgtcgttgt cgttttgtcg tt                                            22

<210> SEQ ID NO 12
<211> LENGTH: 18
<212> TYPE: DNA
<213> ORGANISM: Artificial Sequence
<220> FEATURE:
<223> OTHER INFORMATION: CpG-271, a comparative example of the present
      invention.

<400> SEQUENCE: 12
tcgtcgttgt cgttttgt                                                 18

<210> SEQ ID NO 13
<211> LENGTH: 17
<212> TYPE: DNA
<213> ORGANISM: Artificial Sequence
<220> FEATURE:
<223> OTHER INFORMATION: CpG-272, a comparative example of the present
      invention.

<400> SEQUENCE: 13
gttgtcgttt tgtcgtt                                                   17

<210> SEQ ID NO 14
<211> LENGTH: 15
<212> TYPE: DNA
<213> ORGANISM: Artificial Sequence
<220> FEATURE:
<223> OTHER INFORMATION: CpG-273, a comparative example of the present
      invention.

<400> SEQUENCE: 14
tcgttgtcgt tttgt                                                     15

<210> SEQ ID NO 15
<211> LENGTH: 15
<212> TYPE: DNA
<213> ORGANISM: Artificial Sequence
<220> FEATURE:
<223> OTHER INFORMATION: CpG-2721, a comparative example of the present
      invention.

<400> SEQUENCE: 15
gttgtcgttg tcgtt                                                     15

<210> SEQ ID NO 16
<211> LENGTH: 16
<212> TYPE: DNA
<213> ORGANISM: Artificial Sequence
<220> FEATURE:
<223> OTHER INFORMATION: CpG-2723, a comparative example of the present
      invention.

<400> SEQUENCE: 16
gtgtcgtttt gtcgtt                                                    16

<210> SEQ ID NO 17
<211> LENGTH: 14
<212> TYPE: DNA
<213> ORGANISM: Artificial Sequence
<220> FEATURE:
<223> OTHER INFORMATION: CpG-2724, a comparative example of the present
      invention.

<400> SEQUENCE: 17
gttgtcgttt tgtc                                                      14

<210> SEQ ID NO 18
<211> LENGTH: 12
<212> TYPE: DNA
<213> ORGANISM: Artificial Sequence
<220> FEATURE:
<223> OTHER INFORMATION: CpG-2725, a comparative example of the present
      invention.

<400> SEQUENCE: 18
gttgtcgttt cc                                                        12

```
<210> SEQ ID NO 19
<211> LENGTH: 19
<212> TYPE: DNA
<213> ORGANISM: Artificial Sequence
<220> FEATURE:
<223> OTHER INFORMATION: CpG-2726, a comparative example of the present
      invention.

<400> SEQUENCE: 19
gttgtgcttt tttgtcgtt                                                19

<210> SEQ ID NO 20
<211> LENGTH: 19
<212> TYPE: DNA
<213> ORGANISM: Artificial Sequence
<220> FEATURE:
<223> OTHER INFORMATION: CpG-2728, a comparative example of the present
      invention.

<400> SEQUENCE: 20
gttgtgcttt tttgtgctt                                                19

<210> SEQ ID NO 21
<211> LENGTH: 16
<212> TYPE: DNA
<213> ORGANISM: Artificial Sequence
<220> FEATURE:
<223> OTHER INFORMATION: CpG-2729, a comparative example of the present
      invention.

<400> SEQUENCE: 21
gtcgtttttt gtcgtt                                                   16

<210> SEQ ID NO 22
<211> LENGTH: 13
<212> TYPE: DNA
<213> ORGANISM: Artificial Sequence
<220> FEATURE:
<223> OTHER INFORMATION: CpG-2730, a comparative example of the present
      invention.

<400> SEQUENCE: 22
gttgtcgttt ttt                                                      13

<210> SEQ ID NO 23
<211> LENGTH: 20
<212> TYPE: DNA
<213> ORGANISM: Artificial Sequence
<220> FEATURE:
<223> OTHER INFORMATION: A forward primer of grouper ]-actin used in
      qRT-PCR.

<400> SEQUENCE: 23
gacatggtgc ggtttctctt                                               20

<210> SEQ ID NO 24
<211> LENGTH: 20
<212> TYPE: DNA
<213> ORGANISM: Artificial Sequence
<220> FEATURE:
<223> OTHER INFORMATION: A reverse primer of grouper ]-actin used in
      qRT-PCR.

<400> SEQUENCE: 24
gcctctgctg tgctgatgta                                               20

<210> SEQ ID NO 25
```

<210> SEQ ID NO 25
<211> LENGTH: 20
<212> TYPE: DNA
<213> ORGANISM: Artificial Sequence
<220> FEATURE:
<223> OTHER INFORMATION: A forward primer of grouper TNF-[\]mused in qRT-PCR.

<400> SEQUENCE: 25
ggatctggcg ctactcagac                                               20

<210> SEQ ID NO 26
<211> LENGTH: 20
<212> TYPE: DNA
<213> ORGANISM: Artificial Sequence
<220> FEATURE:
<223> OTHER INFORMATION: A reverse primer of grouper TNF-[\]mused in qRT-PCR.

<400> SEQUENCE: 26
tccgatagct ggttggtttc                                               20

<210> SEQ ID NO 27
<211> LENGTH: 20
<212> TYPE: DNA
<213> ORGANISM: Artificial Sequence
<220> FEATURE:
<223> OTHER INFORMATION: A forward primer of grouper IL-1] used in qRT-PCR.

<400> SEQUENCE: 27
gacatggtgc ggtttctctt                                               20

<210> SEQ ID NO 28
<211> LENGTH: 20
<212> TYPE: DNA
<213> ORGANISM: Artificial Sequence
<220> FEATURE:
<223> OTHER INFORMATION: A reverse primer of grouper IL-1] used in qRT-PCR.

<400> SEQUENCE: 28
gcctctgctg tgctgatgta                                               20

<210> SEQ ID NO 29
<211> LENGTH: 20
<212> TYPE: DNA
<213> ORGANISM: Artificial Sequence
<220> FEATURE:
<223> OTHER INFORMATION: A forward primer of grouper IL-6 used in qRT-PCR.

<400> SEQUENCE: 29
cctgaaggac ctcgacaatc                                               20

<210> SEQ ID NO 30
<211> LENGTH: 20
<212> TYPE: DNA
<213> ORGANISM: Artificial Sequence
<220> FEATURE:
<223> OTHER INFORMATION: A reverse primer of grouper IL-6 used in qRT-PCR.

<400> SEQUENCE: 30
tcctgacagc cagacttcct                                               20

<210> SEQ ID NO 31
<211> LENGTH: 20

-continued

```
<212> TYPE: DNA
<213> ORGANISM: Artificial Sequence
<220> FEATURE:
<223> OTHER INFORMATION: A forward primer of grouper IL-8 used in
      qRT-PCR.

<400> SEQUENCE: 31
gagctgcact gtcgctgtat                                            20

<210> SEQ ID NO 32
<211> LENGTH: 20
<212> TYPE: DNA
<213> ORGANISM: Artificial Sequence
<220> FEATURE:
<223> OTHER INFORMATION: A reverse primer of grouper IL-8 used in
      qRT-PCR.

<400> SEQUENCE: 32
tgttggccat gatcctgtta                                            20

<210> SEQ ID NO 33
<211> LENGTH: 20
<212> TYPE: DNA
<213> ORGANISM: Artificial Sequence
<220> FEATURE:
<223> OTHER INFORMATION: A forward primer of grouper Mx used in
      qRT-PCR.

<400> SEQUENCE: 33
ccatctgacg caactgagaa                                            20

<210> SEQ ID NO 34
<211> LENGTH: 20
<212> TYPE: DNA
<213> ORGANISM: Artificial Sequence
<220> FEATURE:
<223> OTHER INFORMATION: A reverse primer of grouper Mx used in
      qRT-PCR.

<400> SEQUENCE: 34
tccacctcgc aaactctctt                                            20

<210> SEQ ID NO 35
<211> LENGTH: 20
<212> TYPE: DNA
<213> ORGANISM: Artificial Sequence
<220> FEATURE:
<223> OTHER INFORMATION: A forward primer of grouper IFN1 used in
      qRT-PCR.

<400> SEQUENCE: 35
ctgtgtcctt cccgaatcat                                            20

<210> SEQ ID NO 36
<211> LENGTH: 20
<212> TYPE: DNA
<213> ORGANISM: Artificial Sequence
<220> FEATURE:
<223> OTHER INFORMATION: A reverse primer of grouper IFN1 used in
      qRT-PCR.

<400> SEQUENCE: 36
tgcacagtac aggagcgaag                                            20

<210> SEQ ID NO 37
<211> LENGTH: 20
<212> TYPE: DNA
```

```
<213> ORGANISM: Artificial Sequence
<220> FEATURE:
<223> OTHER INFORMATION: A forward primer of grouper IFN gamma used in
      qRT-PCR.

<400> SEQUENCE: 37
gaccaccaag atggaggcta                                          20

<210> SEQ ID NO 38
<211> LENGTH: 20
<212> TYPE: DNA
<213> ORGANISM: Artificial Sequence
<220> FEATURE:
<223> OTHER INFORMATION: A reverse primer of grouper IFN gamma used in
      qRT-PCR.

<400> SEQUENCE: 38
taccggtgtt tcctcaggtc                                          20

<210> SEQ ID NO 39
<211> LENGTH: 20
<212> TYPE: DNA
<213> ORGANISM: Artificial Sequence
<220> FEATURE:
<223> OTHER INFORMATION: A forward primer of grouper CCL4 used in
      qRT-PCR.

<400> SEQUENCE: 39
gtggtactgg cccaaagaaa                                          20

<210> SEQ ID NO 40
<211> LENGTH: 20
<212> TYPE: DNA
<213> ORGANISM: Artificial Sequence
<220> FEATURE:
<223> OTHER INFORMATION: A reverse primer of grouper CCL4 used in
      qRT-PCR.

<400> SEQUENCE: 40
ggctgaaggt ctgacacaca                                          20

<210> SEQ ID NO 41
<211> LENGTH: 20
<212> TYPE: DNA
<213> ORGANISM: Artificial Sequence
<220> FEATURE:
<223> OTHER INFORMATION: A forward primer of mouse gapdh used in
      qRT-PCR.

<400> SEQUENCE: 41
acccagaaga ctgtggatgg                                          20

<210> SEQ ID NO 42
<211> LENGTH: 20
<212> TYPE: DNA
<213> ORGANISM: Artificial Sequence
<220> FEATURE:
<223> OTHER INFORMATION: A reverse primer of mouse gapdh used in
      qRT-PCR.

<400> SEQUENCE: 42
cacattgggg gtaggaacac                                          20

<210> SEQ ID NO 43
<211> LENGTH: 20
<212> TYPE: DNA
<213> ORGANISM: Artificial Sequence
```

```
<220> FEATURE:
<223> OTHER INFORMATION: A forward primer of mouse tnf-[\]mused in
      qRT-PCR.

<400> SEQUENCE: 43
ggatctggcg ctactcagac                                                  20

<210> SEQ ID NO 44
<211> LENGTH: 20
<212> TYPE: DNA
<213> ORGANISM: Artificial Sequence
<220> FEATURE:
<223> OTHER INFORMATION: A reverse primer of mouse tnf-[\]mused in
      qRT-PCR.

<400> SEQUENCE: 44
tccgatagct ggttggtttc                                                  20

<210> SEQ ID NO 45
<211> LENGTH: 20
<212> TYPE: DNA
<213> ORGANISM: Artificial Sequence
<220> FEATURE:
<223> OTHER INFORMATION: A forward primer of mouse il-1] used in
      qRT-PCR.

<400> SEQUENCE: 45
caggcaggca gtatcactca                                                  20

<210> SEQ ID NO 46
<211> LENGTH: 20
<212> TYPE: DNA
<213> ORGANISM: Artificial Sequence
<220> FEATURE:
<223> OTHER INFORMATION: A reverse primer of mouse il-1] used in
      qRT-PCR.

<400> SEQUENCE: 46
agctcatatg ggtccgacag                                                  20

<210> SEQ ID NO 47
<211> LENGTH: 20
<212> TYPE: DNA
<213> ORGANISM: Artificial Sequence
<220> FEATURE:
<223> OTHER INFORMATION: A forward primer of mouse il-6 used in
      qRT-PCR.

<400> SEQUENCE: 47
agttgccttc ttgggactga                                                  20

<210> SEQ ID NO 48
<211> LENGTH: 20
<212> TYPE: DNA
<213> ORGANISM: Artificial Sequence
<220> FEATURE:
<223> OTHER INFORMATION: A reverse primer of mouse il-6 used in
      qRT-PCR.

<400> SEQUENCE: 48
tccacgattt cccagagaac                                                  20

<210> SEQ ID NO 49
<211> LENGTH: 20
<212> TYPE: DNA
<213> ORGANISM: Artificial Sequence
<220> FEATURE:
```

```
<223> OTHER INFORMATION: A forward primer of mouse cxcl1 used in
      qRT-PCR.

<400> SEQUENCE: 49
gctgggattc acctcaagaa                                                   20

<210> SEQ ID NO 50
<211> LENGTH: 20
<212> TYPE: DNA
<213> ORGANISM: Artificial Sequence
<220> FEATURE:
<223> OTHER INFORMATION: A reverse primer of mouse cxcl1 used in
      qRT-PCR.

<400> SEQUENCE: 50
cttggggaca ccttttagca                                                   20

<210> SEQ ID NO 51
<211> LENGTH: 26
<212> TYPE: DNA
<213> ORGANISM: Artificial Sequence
<220> FEATURE:
<223> OTHER INFORMATION: A forward primer for cloning ggTLR21 cDNA.

<400> SEQUENCE: 51
gaacagattc ctgtaccatg ttcatc                                            26

<210> SEQ ID NO 52
<211> LENGTH: 25
<212> TYPE: DNA
<213> ORGANISM: Artificial Sequence
<220> FEATURE:
<223> OTHER INFORMATION: A reverse primer for cloning ggTLR21 cDNA.

<400> SEQUENCE: 52
gcttgtatga attgtcacac tgcac                                             25
```